United States Patent
Kopsky et al.

(10) Patent No.: US 11,147,799 B2
(45) Date of Patent: Oct. 19, 2021

(54) TOPICAL PHARMACEUTICAL COMPOSITION CONTAINING PHENYTOIN AND A (CO-) ANALGESIC FOR THE TREATMENT OF CHRONIC PAIN

(71) Applicants: Topical Innovations B.V., Amsterdam (NL); Jan Marius Keppel Hesselink, Bosch en Duin (NL)

(72) Inventors: David Jos Kopsky, Amsterdam (NL); Jan Marius Keppel Hesselink, Bosch en Duin (NL)

(73) Assignees: Jan Marius Keppel Hesselink, Amsterdam (NL); TOPICAL INNOVATIONS B.V., Amsterdam (NL)

( * ) Notice: Subject to any disclaimer, the term of this patent is extended or adjusted under 35 U.S.C. 154(b) by 0 days.

(21) Appl. No.: 16/467,169

(22) PCT Filed: Dec. 6, 2017

(86) PCT No.: PCT/NL2017/050815
§ 371 (c)(1),
(2) Date: Jun. 6, 2019

(87) PCT Pub. No.: WO2018/106108
PCT Pub. Date: Jun. 14, 2018

(65) Prior Publication Data
US 2020/0069649 A1    Mar. 5, 2020

(30) Foreign Application Priority Data
Dec. 6, 2016   (NL) .................................... 2017932

(51) Int. Cl.
| A61K 31/4166 | (2006.01) |
| A61P 25/02 | (2006.01) |
| A61K 9/00 | (2006.01) |
| A61K 9/06 | (2006.01) |
| A61K 31/135 | (2006.01) |
| A61K 31/197 | (2006.01) |
| A61K 31/451 | (2006.01) |

(52) U.S. Cl.
CPC ........ *A61K 31/4166* (2013.01); *A61K 9/0014* (2013.01); *A61K 9/06* (2013.01); *A61K 31/135* (2013.01); *A61K 31/197* (2013.01); *A61K 31/451* (2013.01); *A61P 25/02* (2018.01)

(58) Field of Classification Search
CPC ........................... A61K 31/4166; A61P 25/02
USPC ......................................................... 514/389
See application file for complete search history.

(56) References Cited

U.S. PATENT DOCUMENTS

| 5,571,521 A | 11/1996 | Lasker |
| 6,387,957 B1 | 5/2002 | Frome |
| 8,470,886 B2 | 6/2013 | King-Smith et al. |
| 9,012,402 B1 | 4/2015 | Blanchard |
| 2004/0076648 A1 | 4/2004 | Williams et al. |
| 2004/0101582 A1 | 5/2004 | Wolicki |
| 2004/0191276 A1 | 9/2004 | Muni |
| 2004/0204366 A1 | 10/2004 | Pasternak et al. |
| 2004/0265364 A1 | 12/2004 | Ozturk et al. |
| 2006/0034910 A1 | 2/2006 | Patel et al. |
| 2009/0022779 A1 | 1/2009 | Kelly et al. |
| 2013/0085171 A1 | 4/2013 | Ray, II et al. |
| 2013/0184351 A1 | 7/2013 | Ciullo |
| 2014/0141056 A1 | 5/2014 | Kubo et al. |

FOREIGN PATENT DOCUMENTS

| CN | 1110141 A | 10/1995 | |
| CN | 101069692 B | 4/2011 | |
| EP | 0193855 B1 | 7/1990 | |
| KR | 10-2012-0086957 A | 8/2012 | |
| WO | 98/07447 A1 | 2/1998 | |
| WO | 01/00191 A2 | 1/2001 | |
| WO | 02/92056 A1 | 11/2002 | |
| WO | WO-2005000241 A2 * | 1/2005 | ............. A61K 47/44 |
| WO | 2006/013084 A1 | 2/2006 | |
| WO | 2008/079727 A2 | 7/2008 | |
| WO | 2010/036937 A1 | 4/2010 | |
| WO | 2015/089050 A1 | 6/2015 | |

OTHER PUBLICATIONS

Yang et al., "Suboptimal Treatment of Diabetic Peripheral Neuropathic Pain in the United States," Pain Medicine, vol. 16, (2015), pp. 2075-2083.
Yajnik et al., Phenytoin as a Coanalgesic in Cancer Pain, Journal of Pain and Symptom Management, Elsevier, vol. 7, No. 4, (1992), XP023115482, pp. 209-213.
Vincent et al., "Biology of Diabetic Neuropathy," Handbook of Clinical Neurology, vol. 115, (2013), pp. 591-606.
Uceyler et al., "Elevated Proinflammatory Cytokine Expression In Affected Skin In Small Fiber Neuropathy," Neurology, vol. 74, (2010), pp. 1806-1813.
Uceyler et al., "Differential Gene Expression of Cytokines and Neurotrophic Factors in Nerve and Skin of Patients With Peripheral Neuropathies," Journal of Neurology, vol. 262, (2015), pp. 203-212.
Uceyler et al., "Differential Expression of Cytokines In Painful And Painless Neuropathies," Neurology, vol. 69, (2007), pp. 42-49.
Tse et al., "Skin Permeability And Pharmacokinetics of Diclofenac Epolamine Administered By Dermal Patch In Yorkshire-Landrace Pigs," Journal of Pain Research, vol. 5, (2012), pp. 401-408.
Serajuddin et al., "Influence of pH on Release of Phenytoin Sodium From Slow-Release Dosage Forms," Journal of Pharmaceutical Sciences, vol. 82, No. 3, (Mar. 1993), pp. 306-310.
Rashidi et al., "The Effect of Phenytoin Cream in Comparison with Betadine Solution on Episiotomy Pain of Primiparous Women," Journal of Caring Sciences, vol. 1, (2012), XP055380888, pp. 61-65.

(Continued)

*Primary Examiner* — Kevin E Weddington
(74) *Attorney, Agent, or Firm* — TraskBritt

(57) ABSTRACT

This disclosure relates to a pharmaceutical composition for topical use wherein the active pharmaceutical ingredient consists of the co-analgesic phenytoin and at least one further co-analgesic, and a method for producing the pharmaceutical composition. In addition, the disclosure relates to the pharmaceutical composition for use in the treatment of chronic pain.

18 Claims, 1 Drawing Sheet

(56) References Cited

OTHER PUBLICATIONS

Rajabally et al., "Hereditary and Inflammatory Neuropathies: A Review of Reported Associations, Mimics and Misdiagnoses," Journal of Neurology Neurosurgery & Psychiatry, vol. 87, (2015), 11 pages.
Petersen et al., "Diclofenac Epolamine (Flector) Patch: Evidence For Topical Activity, Clinical Drug Investigation," vol. 29, No. 1, (2009), 1-9.
Moulin et al., "Pharmacological Management of Chronic Neuropathic Pain: Revised Consensus Statement From the Canadian Pain Society," Pain Research and Management, vol. 19, (2014), pp. 328-335.
Moore et al., "Gabapentin for Chronic Neuropathic Pain and Fibromyalgia in Adults," Cochrane Database of Systematic Reviews, Issue 4, (2014), 124 pages.
Mcquay et al., "Anticonvulsant Drugs For Management of Pain: A Systematic Review," Bmj, vol. 311, (Oct. 21, 1995), pp. 1047-1052.
Lund et al., "Pharmacokinetics of Single and Multiple Doses of Phenytoin in Man," European Journal of Clinical Pharmacology, vol. 7, Issue 2, (Mar. 1974), pp. 81-86.
Korinth et al., "Potential of the Octanol-Water Partition Coefficient (logP) to Predict the Dermal Penetration Behaviour of Amphiphilic Compounds in Aqueous Solutions," Toxicology Letters, vol. 215, (2012), pp. 49-53.
Kopsky et al., "Neuropathic Pain as a Result of Acromegaly, Treated With Topical Baclofen Cream," Journal of Pain Symptom Management, vol. 46, (2013), pp. e4-e5.
Kopsky et al., "High Doses of Topical Amitriptyline in Neuropathic Pain: Two Cases and Literature Review," Pain Practice, vol. 12, (2011), pp. 148-153.
Kopsky et al., "Central Neuropathic Pain In a Patient With Multiple Sclerosis Treated Successfully With Topical Amitriptyline," Case Reports in Medicine, vol. 2012, (2012), Article ID 471835, 3 pages.
Keskin et al., "Doxepin Incorporated into a Dermatologic Cream: an Assessment of Both Doxepin Antipruritic Action and Doxepin Action As An Inhibitor of Papules, In Allergen and Histamine-Caused Pruritus," Allergol Immunopathol (Madr), vol. 27, No. 5, (1999), pp. 265-270.
Jensen et al., "Anticonvulsants in Neuropathic Pain: Rationale And Clinical Evidence," European Journal of Pain, vol. 6, (Suppl. A), (2002), pp. 61-68.
Jay et al., Neuropathic Pain: Etiology, Pathophysiology, Mechanisms, and Evaluations, Disease-a-Month, vol. 60, (2014), pp. 6-47.
Hesselink et al., "Vulvodynia and Proctodynia Treated With Topical Baclofen 5 % and Palmitoylethanolamide," Archives of Gynecology Obstet, vol. 290, (2014), pp. 389-393.
Hesselink et al., "Treatment of Chronic Regional Pain Syndrome Type 1 With Palmitoylethanolamide and Topical Ketamine Cream: Modulation of Nonneuronal Cells," Journal of Pain Research, vol. 6, (2013), pp. 239-245.
Hearn et al., "Desipramine for Neuropathic Pain in Adults," Cochrane Database of Systematic Reviews, vol. 9, (2014), 33 pages.
Glinn et al., "Urinary Concentrations of Topically Administered Pain Medications," Journal of Analytical Toxicology, vol. 41, (2016), pp. 127-133.
Gharibian et al., "Compliance and Persistence of Antidepressants Versus Anticonvulsants in Patients With Neuropathic Pain During the First Year of Therapy," Clinical journal of pain, vol. 29, (2013), pp. 377-381.
Finnerup et al., "Pharmacotherapy for Neuropathic Pain in Adults: A Systematic Review and Meta-Analysis," Lancet Neurology, vol. 14, (2015), pp. 162-173.
Ellis et al., "Neuroinflammation and the Generation of Neuropathic Pain," British Journal of Anaesthesia, vol. 111, (2013), pp. 26-37.
Derry et al., "Topical Lidocaine for Neuropathic Pain in Adults," Cochrane Database of Systematic Reviews, Issue 7, (2014), 12 pages.
David J. Kopsky, "Phenytoin in Topical Formulations Augments Pain Reduction of Other Topically Applied Analgesics in the Treatment of Trigeminal Neuralgia," Journal of Clinical Anesthesia, vol. 38, (2017), XP029963147, pp. 154-155.
Database WPI CN1110141, Oct. 18, 1995, XP002778531.
Callaghan et al., "The Importance of Rare Subtypes in Diagnosis and Treatment of Peripheral Neuropathy: A Review," JAMA Neurology, vol. 72, (2015), pp. 1510-1518.
Bos et al., "The 500 Dalton Rule For The Skin Penetration of Chemical Compounds And Drugs," Experimental Dermatology, vol. 9, (2000), pp. 165-169.
Baron et al., "Peripheral Input and Its Importance for Central Sensitization," Annals of Neurology, vol. 74, (2013), pp. 630-636.
Bailey DN., "Percutaneous Absorption of Tricyclic Antidepressants: Amitriptyline, Nortriptyline, Imipramine, and Desipramine," Journal of Analytical Toxicology, vol. 14, No. 4, (1990), pp. 217-218.
Babaei et al., "Enhanced Skin Penetration of Lidocaine Through Encapsulation into Nanoethosomes and Nanostructured Lipid Carriers: A Comparative Study," Pharmazie, vol. 71, No. 5, (2016), pp. 247-251.
Alan Israel, "Topical Gel for the Treatment of a Refractory Leg Ulcer", International Journal of Pharmaceutical Compounding, vol. 7, No. 3, (2003), XP055380945, 3 pages.
Barton et al. "A double-blind, placebo-controlled trial of a topical treatment for chemotherapy-induced peripheral neuropathy: NCCTG trial N06CA" Support Care Cancer Jun. 2011; 19(6) 833-841, DOI 10.1007/s00520-010-0911-0.
Brutcher et al. "Compounded Topical Pain Creams to Treat Localized Chronic Pain: A Randomized Controlled Trial" Ann Intern Med. Mar. 5, 2019;170(5):309-318.
Coderre "Topical drug therapeutics for neuropathic pain" Expert Opin Pharmacother. 2018.
European Communication pursuant to Article 94(3) EPC for European Application No. 17817292, dated Jul. 30, 2020, 6 pages.
Gewandter et al. "A phase III randomized, placebo-controlled study of topical amitriptyline and ketamine for chemotherapy-induced peripheral neuropathy (CIPN): a University of Rochester CCOP study of 462 cancer survivors" Support Care Cancer. Jul. 2014;22(7):1807-14.
Lynch et al. "A pilot study examining topical amitriptyline, ketamine, and a combination of both in the treatment of neuropathic pain" The Clinical Journal of Pain, 2003, 19: 323-328.
Lynch et al. "Topical 2% amitriptyline and 1% ketamine in neuropathic pain syndromes" Anesthesiology, 2005, 103(1): p. 140-146.).
McCleane "Topical application of doxepin hydrochloride, capsaicin and a combination of both produces analgesia in chronic human neuropathic pain: a randomized, double-blind, placebo-controlled study" Br J Clin Pharmacol. Jun. 2000;49(6):574-9.
Somberg et al. "Retrospective Study on the Analgesic Activity of a Topical (TT-CTAC) Cream in Patients With Diabetic Neuropathy and Other Chronic Pain Conditions" American Journal of Therapeutics 22, 214-221 (2015).

* cited by examiner

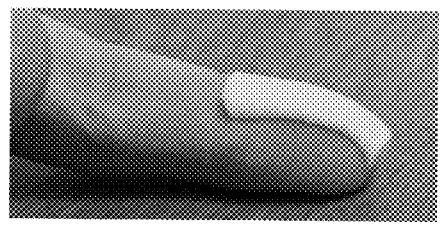

TOPICAL PHARMACEUTICAL COMPOSITION CONTAINING PHENYTOIN AND A (CO-) ANALGESIC FOR THE TREATMENT OF CHRONIC PAIN

CROSS-REFERENCE TO RELATED APPLICATIONS

This application is a national phase entry under 35 U.S.C. § 371 of International Patent Application PCT/NL2017/050815, filed Dec. 6, 2017, designating the United States of America and published in English as International Patent Publication WO 2018/106108 A1 on Jun. 14, 2018, which claims the benefit under Article 8 of the Patent Cooperation Treaty to Dutch Patent Application Serial No. 2017932, filed Dec. 6, 2016.

TECHNICAL FIELD

This disclosure relates to a pharmaceutical composition for topical use wherein the active pharmaceutical ingredient consists of the co-analgesic phenytoin and at least one further co-analgesic, and a method for producing the pharmaceutical composition. In addition, the disclosure relates to the pharmaceutical composition for use in the treatment of chronic pain.

BACKGROUND

Pain results from noxious stimulation of nerve endings. Nociceptive pain is caused by noxious stimulation of nociceptors that transmit impulses over intact neural pathways to the spinal neurons and then to the brain. The International Association for the Study of Pain (IASP 2011, www.iasp-pain.org/Taxonomy?#Neuropathicpain) defines neuropathic pain as: "Pain caused by a lesion or disease of the somatosensory nervous system."

Peripheral neuropathic pain is pain due to damage of the nerve endings, mostly found in the skin, especially in the epidermis. These damaged nerve endings can generate impulses in the absence of stimulation, can be hypersensitive to normal stimulation, and/or can be triggered by remaining local inflammatory stimulation. Even a very small number of damaged and overactive small nerve fibers in the epidermis are sufficient to trigger peripheral neuropathic pain. Neuropathic pain can be debilitating and can reduce quality of life of patients considerably. This pain may persist for months or years beyond the apparent healing of any damaged tissues.

Neuropathic pain has a local inflammatory component that results in sensitization of nerve fibers. Other intact nerve fibers, such as nociceptors being present up in the stratum granulosum, innervating the same region can also be sensitized and participate in clinical symptoms of neuropathic pain (e.g., hyperalgesia). This results in a situation of local neurogenic inflammation resulting in many different clinical features such as burning, freezing, electric shock, itch, tingling, pins and needles, hyperalgesia and allodynia (pain resulting from a non-painful stimulus such as a light touch or stroke).

Peripheral nerve damage leads to enhanced transmitter release within the spinal cord and can lead to central sensitization (Baron R, et al., 2013). Increased peripheral input through primary afferents is critically involved in central sensitization and the maintenance of neuropathic pain. Peripherally acting drugs, such as lidocaine 5% medicated patches and capsaicin 8% patches, have demonstrated the ability to reduce pain in neuropathic pain syndromes (Baron R, et al., 2013). However, lidocaine patches are not easy to apply, especially on the toes and by elderly, because the patch has to be cut, and many elderly cannot reach their toes properly. Application of capsaicin creams and patches quite often induce intolerable side effects, such as an increase of burning sensation, and often the treatment has to be combined with a local anesthetic to neutralize this side effect.

Without wishing to be bound by theory, it was postulated that the aforementioned pathogenic pathways in the skin are at least influenced, perhaps even dominated by inflammatory processes leading to chronification of pain after a peripheral nerve injury and/or after local intra- or sub-epidermal pathologies. Even discrete pathologies in the skin such as a small number of overactive aberrant small nerve fibers can already trigger peripheral neuropathic pain.

In chronic pain in general, for instance, oral analgesics such as acetaminophen, nonsteroidal anti-inflammatory drugs (NSAIDs) and opioids are part of guidelines aimed at to reduce the pain. Chronic use of such oral analgesics however, can induce serious and mortal side effects and/or detrimental drug-drug interactions.

The treatment of neuropathic pain is also cumbersome. All prescribed treatments focus only on the pain modality of neuropathy. Thus all literature focuses on analgesics and the only goal of treatment is defined as full or partial analgesia. Furthermore, only a few classes of analgesics and co-analgesics are introduced in the guidelines and treatment schedules for neuropathic pain. Oral antidepressants (e.g., amitriptyline, duloxetine) and anticonvulsants (e.g., pregabalin, gabapentin) are the first choice treatments for neuropathic pain, capsaicin patches are second choice and opioids (e.g., tramadol, oxycodone) are third choice (Finnerup N B et al., 2015). Unfortunately, for many analgesics the evidence for efficacy in neuropathic pain indications is also widely debated, or even absent. For instance, a recent meta-analysis found little evidence to support the use of desipramine to treat neuropathic pain (Hearn et al., 2014). Even for the most often prescribed compounds such as gabapentin and pregabalin, evidence of efficacy is not of top tier level (Moore et al., 2014). Only about 35% of the patients achieved 50% or more pain relief with gabapentin, compared with 21% for placebo (Moore et al., 2014). The majority of patients is not compliant with the prescribed analgesics in the first year of therapy and up to half of the patients stop within 3 months, probably due to minimal pain relief and/or intolerable side effects, including sedation, dizziness, depression, nausea and constipation and feeling like a zombie (Gharibian D et al., 2013; Yang M et al., 2015). This makes clear that there is a significant and urgent need for new analgesics for use in the treatment of chronic pain and neuropathic pain.

Topical painkiller pharmaceutical compositions are also explored to help patients suffering from chronic pain. Two most commonly used topical compounds in neuropathic pain are capsaicin (vanilloid receptor agonist and counter-irritant) and lidocaine (membrane stabilizer), and both have clear drawbacks.

Topical capsaicin 0.025% to 0.075% as well as capsaicin 8% patch however, indeed have the disadvantage that application often induces intolerable side effects, such as increasing of burning sensation, and often the treatment has to be combined with a local anesthetic to neutralize this side-effect (Jay G W and Barkin R L, 2014). The topical lidocaine 5% medicated patch, disclosed in U.S. Patent Application 2014/0141056 and U.S. Patent Application 2013/0184351 needs to be replaced every 12 hours, cannot be used on wounds, ulcers, damaged or inflamed skin, commonly seen in patients with diabetic neuropathy, and regularly gives problems when applied to the toes, especially in elderly, because the patch has to be cut.

Other analgesic or co-analgesic compounds in topical pharmaceutical compositions have been described and used for the treatment of neuropathic pain, mostly prepared by a compounding pharmacist. For instance, topical ketamine, alone or in combination with amitriptyline and/or guanethidine for various neuropathies to achieve regional pain relief is disclosed in U.S. Pat. No. 6,387,957. In international Patent Application WO 98/07447 the topical use of an anticonvulsant combined with a nontoxic NMDA receptor antagonist is described, with the possibility of adding a third compound from the group of acetaminophen or NSAIDs, for the treatment of neuropathic pain. In international Patent Application WO 2010/036937 the topical use for the treatment of neuropathic pain of an NMDA receptor antagonist combined with gabapentin to reduce the risk of side effects of the former compound, is disclosed. In U.S. Patent Application 20040204366 the combination of opioids (e.g., morphine) and local anesthetics (e.g., lidocaine) is disclosed. In U.S. Patent Application 2004/0265364 the combination of topical amitriptyline, clonidine, ketamine and ketoprofen is disclosed. In U.S. Patent Application 2004/0101582 the combination of ketamine, gabapentin and clonidine with a possible other active compound to increase the analgesic effectiveness, such as baclofen, capsaicin, loperamide, nifedipine or pentoxifylline, is disclosed. The U.S. Patent Application 2004/0076648 discloses a stable cream with good penetrations properties for an antidepressant and a NMDA receptor antagonist. Another strategy disclosed in U.S. Patent Application 2013/0085171 is a cream base that can deliver at least 30% of the therapeutically active compounds.

None of these aforementioned creams, however, reached the market and became part of neuropathic pain treatment guidelines. This is likely due to various drawbacks, such as suboptimal stability in the vehicles selected, suboptimal combinations and concentrations and short duration of the analgesic effects.

Several topical pharmaceutical compositions for use in the treatment of musculoskeletal pain have been disclosed. For example, U.S. Pat. No. 9,012,402 discloses a topical analgesic pharmaceutical compositions with ketoprofen, a skin penetration enhancer, a thickening agent and a base to adjust pH to provide relief of inflammation and pain in rheumatoid arthritis, osteoarthritis, soft tissue injuries. In U.S. Pat. No. 8,470,886 a topical formulation comprising ibuprofen in a hydroalcoholic-based solvent system containing triethyl acetate and a surfactant is disclosed.

The clinical response to these topical treatments, however, is not convincing, and such formulations did not yet find its way into treatment guidelines.

Phenytoin, also known as diphenylhydantoin (DILANTIN®), is the generic name of 5,5-diphenyl-2,4-imidazolidinedione. Phenytoin is generally seen as a first generation anticonvulsant, synthesized in 1908 and found to be an active anticonvulsant in 1936. Phenytoin has been widely used as an anticonvulsant since its clinical introduction in 1938. Despite this, its molecular mechanism of action is not fully understood and surprisingly quite different new indications have emerged since its use as an anticonvulsant, such as wound healing and bipolar depression. It is felt that the multiplicity of the pharmacological effects of phenytoin on ion channels and synaptic transmission, cannot explain all its actions as an anticonvulsant. Other effects have been looked for, such as neuroprotective properties, influences in gene expression, and effects on short-term plasticity at excitatory synapses to mention a few.

Oral phenytoin, however, did not result in convincing efficacy as an analgesic and was never taken up in treatment guidelines. For instance, two cross-over clinical trials in diabetic neuropathic pain show conflicting results (McQuay H et al., 1995). The use of oral phenytoin for the treatment of chronic neuropathic pain, is clearly limited due to its absence of proven analgesic effects and its side effects (which includes sedation and motor disturbances) and complicated pharmacokinetic profile (Jensen T S, 2002).

The known use of topical phenytoin can be found solely in the enhancement of wound healing as disclosed in U.S. Patent Application 2009/0022779. Topical phenytoin has been described to have antibacterial properties, as disclosed in U.S. Pat. No. 5,571,521.

Clearly, there remains a pressing and long felt need in the art of developing treatment options for chronic pain in general and neuropathic pain, in particular, for the development of a novel and effective pharmaceutical composition for use in the treatment of chronic pain, the composition inflicting less side effects to the patient.

BRIEF SUMMARY

A completely new use for phenytoin was surprisingly found. That is to say, phenytoin acts as a co-analgesic compound boosting the analgesic effect of yet at least one further (co-)analgesic compound in a pharmaceutical composition for topical use, used in the treatment of chronic pain.

It has surprisingly been discovered that when the co-analgesic phenytoin, or a derivative, prodrug, stereoisomer, and/or salt thereof, is combined with yet at least one other (co-)analgesic compound, a so-called booster effect, or synergistic effect, is achieved with regard to the efficacy in the treatment of chronic pain in a patient when the combined compounds are topically administered. This booster effect thus surprisingly encompasses: 1) an enhanced therapeutic effect of the active pharmaceutical ingredient, i.e., at least one (co-)analgesic compound, the enhanced therapeutic effect of which aids in alleviating neuropathic pain, inflammatory pain, musculoskeletal pain, pain due to muscle spasms, and/or other chronic pain states with improved efficacy and to a more satisfactory extent, 2) a faster onset of pain relieving effect, 3) a longer duration of analgesia, and/or 4) reinstating analgesic effects, when decreasing analgesic effect occurred after repeated use of a topical pharmaceutical composition containing at least one analgesic compound or co-analgesic compound.

A first aspect of the disclosure is a pharmaceutical composition wherein the active pharmaceutical ingredients consist of:
  a) a first co-analgesic selected from phenytoin or a derivative, a prodrug, a stereoisomer, and/or a salt thereof, or any combination thereof, and
  b) at least one further (co-)analgesic,
and further containing a pharmaceutically acceptable carrier for topical use.

One embodiment of the disclosure is the pharmaceutical composition of the disclosure, wherein the first co-analgesic is phenytoin, phenytoin sodium or a combination thereof.

One embodiment of the disclosure is the pharmaceutical composition of the disclosure, wherein the first co-analgesic of a) is phenytoin or phenytoin sodium or the combination thereof, and wherein the at least one further (co-)analgesic of b) is selected from baclofen, clonidine, loperamide and isosorbide dinitrate, or wherein the at least one further (co-)analgesics of b) are the combination of baclofen and amitriptyline, or loperamide and amitriptyline, or baclofen and loperamide.

One embodiment of the disclosure is the pharmaceutical composition of the disclosure, wherein the first co-analgesic of a) is phenytoin or phenytoin sodium or the combination thereof, and wherein the at least one further (co-)analgesic of b) is isosorbide dinitrate.

A second aspect of the disclosure is a method for preparing a pharmaceutical composition for use in the treatment of chronic pain according to the disclosure, comprising the steps of:

a. providing oil-soluble constituents and separately providing water soluble constituents of a pharmaceutically acceptable carrier for topical use;
b. providing a first co-analgesic selected from phenytoin or a derivative, a prodrug, a stereoisomer, and/or a salt thereof, preferably phenytoin or phenytoin sodium or a combination thereof, and providing at least one further (co-)analgesic;
c. mixing the oil-soluble constituents at between 20° C. to 95° C. of step a. by stirring, and separately, dissolving the water-soluble constituents of step a. in water, wherein the water is optionally heated to between 20° C. to 95° C. while dissolving the water-soluble constituents of step a., thereby providing an aqueous solution;
d. combining the mixed oil-soluble constituents of step c. with the aqueous solution of step c., wherein the temperature of the mixed oil-soluble constituents and the aqueous solution is about the same, preferably about 70° C., and mixing by stirring, thereby providing the pharmaceutically acceptable carrier for topical use;
e. mixing the (co-)analgesics of step b. with the pharmaceutically acceptable carrier of step d. by adding the (co-)analgesics of step b. to the carrier while stirring for between 5 to 20 minutes, preferably for about 10 minutes, wherein the temperature of the (co-)analgesics and of the pharmaceutically acceptable carrier is preferably room temperature, preferably about 20° C. while mixing; and
f. optionally adjusting the pH of the pharmaceutical composition to between 4.0 and 6.5.

A third aspect of the disclosure is a pharmaceutical composition for use in the treatment of chronic pain according to the disclosure, wherein the chronic pain is neuropathic pain, peripheral neuropathic pain, inflammatory pain, musculoskeletal pain, pain due to muscle spasms, pain due to increased muscle tone, osteoarthritic pain, muscular headache, tension-type headache, migraine, cluster headache, atypical facial pain, referred pain, vulvodynia, proctodynia, or combinations thereof.

In one embodiment, the pharmaceutical composition for use in the treatment of chronic pain according to the disclosure, is the composition wherein the first co-analgesic is between 5% and 10%, and wherein the at least one further (co-)analgesic is selected from about 10% ketamine, about 5% baclofen, about 0.2% clonidine, about 5% loperamide, about 5% lidocaine and about 0.4% isosorbide dinitrate, or wherein the at least one further (co-)analgesics are the combination of about 5% baclofen and about 5% amitriptyline, or ketamine 10% and amitriptyline 5%, or loperamide 5% and baclofen 5% by weight of the pharmaceutical composition. Preferred is, for example, the pharmaceutical composition for use in the treatment of chronic pain according to the disclosure, wherein the first co-analgesic is 5% phenytoin by weight of the composition and wherein the second (co-)analgesic is 10% amitriptyline by weight of the composition. Treatment of a patient suffering from chronic pain prolonged the duration of the analgesic effect substantially so that the duration of the pain-killing effect was even about tripled when the amount of phenytoin was raised to 10% by weight of the composition. In contrast, for example, in the prior art, an increase of the content of ketamine from 15% to 30% in a composition, while the content of gabapentin was kept at 6% in the composition, did not result in an improved analgesic effect obtainable with this composition, i.e., the duration of the pain relief remained unaltered under influence of doubling the concentration of ketamine in the composition of the prior art.

Definitions

Unless defined otherwise, all technical and scientific terms used herein have the same conventional meaning as commonly understood by one of ordinary skill in the art to which this disclosure belongs.

The term "comprising" or "comprises" as used herein has its conventional meaning and here means that the list following is non-exhaustive and may or may not include any other additional suitable items, for example, one or more further feature(s), component(s) and/or ingredient(s) as appropriate.

The term "approximately" as used herein has its conventional meaning and here means that a certain effect or result can be obtained within a certain tolerance that the skilled person knows how to obtain, and here indicates a reasonable amount of tolerated deviation of the identified parameter value such that the end result is not significantly changed. This reasonable amount of deviation should be construed as including a deviation of at least ±5% of the identified parameter value, as long as this deviation does not negate the end result.

The term "chronic pain" or "chronic pain states" as used herein, is defined as any pain lasting longer than 12 weeks.

The term "neuropathic pain" as used herein has its conventional meaning and here means a pain arising as a direct or indirect consequence of a lesion or disease affecting the somatosensory system (central and/or peripheral). Neuropathic pain as used herein, includes all types of neuropathic pain, such as peripheral neuropathy caused by diabetes type 1 or 2, induced by various noxious substances such as alcohol, due to various deficiencies such as vitamin B1, B6 and/or B12 deficiency, various intoxications, such as hypervitaminosis B6, hypothyroidism, chemotherapeutic compound (e.g., paclitaxel or other taxane derivative, vincristine or other vinca alkaloids, cisplatin or other platinum derivate), drug-induced neuropathy, compounds for the treatment of infectious diseases (e.g., streptomycin, didanosine or zalcitabine), or any other chemically toxic compound. Other peripheral neuropathies include the following: trigeminal neuralgia, post-herpetic neuralgia, intercostal neuralgia, entrapment neuropathy (e.g., carpal tunnel syndrome, tarsal tunnel syndrome, abdominal cutaneous nerve entrapment syndrome), small fiber neuropathy, hereditary motor and sensory neuropathies, chronic inflammatory demyelinating polyneuropathy, sciatic pain chronic idiopathic sensory neuropathy, infectious disease conditions such as post-polio syndrome, AIDS or HIV-associated, Lyme-associated, Sjögren-associated, lymphomatous neuropathy, myelomatous neuropathy, carcinomatous neuropathy, acute pan autonomic neuropathy, vasculitic/ischaemic neuropathy and other mono- and polyneuropathies. Furthermore, under the term "neuropathic pain" also the following is included: complex regional pain syndrome type I and II (reflex sympathetic dystrophy), central neuropathic pain (e.g., thalamic neuropathy, spinal cord injury neuropathy, post stroke pain, multiple sclerosis neuropathy, syringomyelia, spinal cord tumors), phantom limb pain, restless genital syndrome (pain), post-surgical scar pain including cardiac surgery and mastectomy.

The term "inflammatory pain" as used herein has its conventional meaning and here means a pain that arises from inflammation that may be caused but by not limited to trauma, burns, extreme cold, fractures, (osteo)arthritis, rheumatoid arthritis, chronic strains, surgery, infection and auto-immune diseases excessive stretching, infections and vasoconstriction. Multiple inflammatory mediators can directly affect nociceptors or may sensitize them to touch or movement, even some distance from the inflammatory field.

The term "musculoskeletal pain" as used herein has its conventional meaning and here means a pain that affects the muscles, ligaments, tendons, bones, joints and/or soft tissues that are part of the musculoskeletal system. Musculoskeletal pain as used herein, includes all types of pain due to damage of muscle tissue as a result of wear and tear of daily activities. Trauma to an area (jerking movements, auto accidents, falls, sport injuries, fractures, sprains, strains dislocations, and direct blows to the muscle) also can cause musculoskeletal pain. Other causes of musculoskeletal pain include postural strain, repetitive movements, overuse, and prolonged immobilization, misuse of muscles, fibromyalgia, lumbar pain, pain due to increased muscle tone, and tendinitis due to overuse.

The term "treatment" as used herein has its conventional meaning and is here to be considered in its broadest context. The term "treatment" is intended to encompass topical administration of active compounds, i.e., active pharmaceutical ingredients e.g., in a pharmaceutical composition, according to the disclosure, with the aim to alleviate an undesired condition, and therapeutic administration to eliminate or reduce the extent or symptoms of the condition. Treatment does not necessarily imply that a subject is treated until total recovery.

The term "analgesic" or "analgesics" as used herein has its conventional meaning and here refers to compounds, agents, drugs or substances that reduce pain in its broadest context.

The term "co-analgesic" or "co-analgesics" as used herein has its conventional meaning and here refers to compounds, agents, drugs or substances whose primary indication is for a purpose other than pain relief, which compounds demonstrate analgesic activity.

The term "reinstating analgesic effects" as used herein has its regular scientific meaning and is here referring to the capability (of a compound or of a composition) of reinstating an analgesic effect of at least one analgesic compound or at least one co-analgesic compound, when decreasing analgesic effect occurs after repeated use of a topical formulation containing at least one analgesic or co-analgesic compound.

The term "effect booster" or "co-analgesic effect booster" or "therapeutic effect booster" or "booster effect" or "synergistic effect" as used herein has its conventional meaning and here means the enhancement of a therapeutic effect induced by a co-analgesic compound ("co-analgesic") leading to 1) intensified therapeutic effects of an active pharmaceutical ingredient with the purpose of alleviating neuropathic pain, inflammatory pain, musculoskeletal pain, pain due to muscle spasms, and/or other chronic pain states, 2) a faster onset of pain relieving effect, 3) a longer duration of analgesia, and/or 4) reinstating analgesic effects, when decreasing analgesic effect occurs after repeated use of a topical pharmaceutical composition containing at least one analgesic compound ("analgesic") or co-analgesic compound.

The term "topical formulation" as used herein has its conventional meaning and here refers to a formulation that may be applied to skin or mucosa with the aim that a therapeutically active compound penetrates in and/or through the skin, e.g., a topical pharmaceutical composition of the disclosure, e.g., a pharmaceutical composition provided as a topical cream.

The term "epidermal formulation" as used herein refers to a topical formulation wherein the active pharmaceutical ingredient is not detectable in plasma, or is detectable to a lesser extent in plasma when compared to a different route of administration than topical administration of an epidermal formulation.

The term "active compound" or "active pharmaceutical ingredient(s)" as used herein has its conventional meaning and here refers to an agent, active ingredient or other substance, or compositions and mixture thereof that provide some pharmacological, often beneficial, effect. In the context of the disclosure, the effect is a reduction in (neuropathic) pain, reduction in non-pain neuropathic sensations, more rapid therapeutic onset of effect, prolonging the duration of the therapeutic effect, and/or intensifying the therapeutic effects. Reference to a specific active compound encompasses the pharmaceutically acceptable salts thereof, prodrugs thereof, and derivatives thereof, unless stated otherwise.

The phrase "derivative, prodrug, stereoisomer, and/or salt thereof" is intended to convey any pharmaceutically acceptable tautomer, salt, pro-drug, hydrate, solvate, metabolite or other compound that, upon administration to a subject, e.g., a patient, is capable of providing (directly or indirectly) the active compound concerned or a physiologically (e.g., analgesically) active compound, metabolite or residue thereof.

The term "solvate" as used herein has its conventional meaning and here refers to a complex of solute (e.g., active compound, salt of active compound) and solvent.

The term "derivative" is a compound that is derived from a similar compound by a chemical reaction. A "derivative" includes esters, amides and protonated forms of these agents. Derivatives of phenytoin are known in the art and, for example, encompass phenytoin-3-histidine (IUPAC name (S)-3-(2-amino-3-(1H-imidazol-4-yl) propanoyl)-5,5-diphenylimidazolidine-2,4-dione), the phenytoin derivatives such as those disclosed in U.S. Pat. No. 5,306,617, hybrids between phenytoin and thiosemicarbazide, 1,3,4-oxadiazole, 1,3,4-thiadiazole or 1,2,4-triazole, phenytoin with any one or more of the substituents selected from the group consisting of: diphenylmethane, 5-phenylhydantoin, phenylimidazolidine, alpha-amino acid or derivatives, 5-mono-substituted hydantoin, N-acyl urea, ureide, a monocyclic benzene moiety, benzenoid, dicarboximide, a carbonic acid derivative, a carboxylic acid derivative, azacycle, a hydrocarbon derivative, an organic oxide, an organo-oxygen compound, an organo-nitrogen compound, an organopnictogen compound, an organic oxygen compound, a carbonyl group, an organic nitrogen compound, and an aromatic heteromonocyclic compound (see, for example, www.drugbank.ca/drugs/DB00252), to name a few phenytoin derivatives known by the person having ordinary skill in the art.

The term "prodrug" as used herein has its conventional meaning and here refers in its broadest sense to include those compounds that can be converted in vivo to the active compound of interest (e.g., by enzymatic or hydrolytic cleavage). Examples thereof include esters, such as acetates of hydroxy or thio groups, as well as phosphates and sulphonates. Processes for acylating hydroxy or thio groups are known in the art, e.g., by reacting an alcohol (hydroxy group), or thio group, with a carboxylic acid.

The term "phenytoin or a derivative, prodrug, stereoisomer, and/or salt thereof" as used herein, refers to phenytoin, fosphenytoin, hydroxyphenytoin, 5-(3-hydroxyphenyl)-5-phenylhydantoin, 5-phenyl-5-(4-hydroxyphenyl)hydantoin glucuronide, ropitoin, ropitoin hydrochloride, 5-(2-hydroxyphenyl)-5-phenylhydantoin, 5-(3,4-dihydroxy-1,5-cyclohexadien-1-yl)-5-phenylhydantoin, N-aminodiphenylhydantoin, 5-(3,4-dihydroxyphenyl)-5-phenylhydantoin, PC-796, 5-p-methylphenyl-5-phenylhydantoin, 1-acetyl-3-acetoxy-5',5-diphenylhydantoin, 3-hydroxymethylphenytoin N,N-dimethylglycine ester, 3-(hydroxymethyl)phenytoin N,N-dimethylaminoethyl carbonate, 5-(4-hydroxy-3-methoxyphenyl)-5-phenylhydantoin, 3-pentanoyl-5,5-diphenylhydantoin, 3-(2-propylpentanoyl)-5,5-diphenylhydantoin, 5,5-bis(4-hydroxyphenyl)hydantoin, 3-(hydroxymethyl)phenytoin, phenytoin dihydrodiol, 4-aminophenytoin, N,N-dichlorophenytoin, diphenylthiohydantoin, diphenylhydantoin-3-phenyltricarbonylchromium ethyl acetate, 5,5-diphenylhydantoin-3-valerate-bovine serum albumin, phenytoin-1-methylnicotininate, 2-cyanoguanidinophenytoin, phenytoin-bis-hydroxyisobutyrate, N-acetylphenytoin, diphenylhydantoic acid, N'-3-oxymethylglucuronide phenytoin, diphenylhydantil, 5-(4'-fluorophenyl)-5-phenylhydantoin, azumolene, 5,5-bis(4-trifluoromethylphenyl)hydantoin, 5,5-bis(4-methylphenyl)hydantoin, 5,5-bis(4-methoxyphenyl)hydantoin, 5-(4-methoxyphenyl)-5-phenylhydantoin, and 5-(4-dimethylaminophenyl)-5-phenylhydantoin, and other 5,5-diphenylimidazolidine or a derivative, prodrug, stereoisomer, and/or salt thereof, such as phenytoin sodium.

The term "muscle relaxant" as used herein has its conventional meaning and here refers to active pharmaceutical ingredients such as baclofen, dantrolene, tizanidine, carisoprodol, cyclobenzaprine or a derivative, prodrug, stereoisomer, and/or salt thereof.

The term "tricyclic antidepressant" as used herein has its conventional meaning and here refers to at least amineptine, amitriptyline, amitriptylinoxide, butriptyline, demexiptiline, dibenzepin, dimetacrine, dothiepin, fiuacizine, iprindole, clomipramine, desipramine, desmethylamitriptyline, doxepin, imipramine, imipraminoxide, trimipramine, lofepramine, maprotiline, melitracen, metapramine, norclolipramine, nortriptyline, noxiptilin, opipramol, perlapine, pizotyline, propizepine, protriptyline, quinupramine, reboxetine, tianeptine or a derivative, prodrug, stereoisomer, and/or salt thereof.

The term "tetracyclic antidepressant" as used herein has its conventional meaning and here refers at least to amoxapine, aptazapine, ciclazindol, esmirtazapine, loxapine, mazindol, metralindole, maprotiline, mianserin, mirtazapine, oxaprotiline, pirlindole, setiptiline or a derivative, prodrug, stereoisomer, and/or salt thereof.

The term "alpha 2-adrenergic agonist" as used herein has its conventional meaning and here refers at least to amidephrine, amitraz, anisodamine, apraclonidine, brimonidine, cirazoline, clonidine, detomidine, dexmedetomidine, epinephrine, ergotamine, etilefrine, fadolmidine, guanabenz, guanethidine, guanfacine, guanoxabenz, indanidine, lofexidine, medetomidine, mephentermine, metaraminol, methoxamine, methyldopa, mivazerol, naphazoline, norepinephrine, norfenefrine, octopamine, oxymetazoline, phenylpropanolamine, rilmenidine, romifidine, synephrine, talipexole, xylazine or a derivative, prodrug, stereoisomer, and/or salt thereof.

The term "selective serotonin reuptake inhibitor" as used herein has its conventional meaning and here refers at least to cericlamine, citalopram, dapoxetine, escitalopram, fluoxetine, fluvoxamine, indalpine, paroxetine, sertraline, zimelidine, or a derivative, prodrug, stereoisomer, and/or salt thereof.

The term "serotonin-noradrenalin reuptake inhibitor" as used herein has its conventional meaning and here refers at least to duloxetine, desvenlafaxine, levomilnacipran, milnacipran, sibutramine, venlafaxine or a derivative, prodrug, stereoisomer, and/or salt thereof.

The term "Non-steroidal anti-inflammatory drug" or "NSAID or NSAIDs" as used herein has its conventional meaning and here refers at least to any non-steroidal anti-inflammatory drug. Non-limiting examples include but are not limited to aceclofenac, acetylsalicylic acid, celecoxib, clonixin, dexibuprofen, dexketoprofendiclofenac, diflunisal, droxicam, etodolac, etoricoxib, fenoprofen, firocoxib, flufenamic acid, flurbiprofen, ibuprofen, indomethacin, isoxicam, ketoprofen, ketorolac, licofelone, lornoxicam, loxoprofen, lumiracoxib, meclofenamic acid, mefenamic acid, meloxicam, nabumetone, naproxen, nimesulide, oxaprozin, parecoxib, piroxicam, phenylbutazone, rofecoxib, salicylic acid, salsalate, sulindac, tenoxicam, tolfenamic acid, tolmetin, and vladecoxib or a derivative, prodrug, stereoisomer, and/or salt thereof.

The terms "opioid, opioids, or opioid receptor agonist" as used herein has its conventional meaning and here include but is not limited to alfentanil, allylprodine, alphaprodine, anileridine, benzyl-morphine, bezitramide, buprenorphine, butorphanol, clonitazene, codeine, cyclazocine, desomorphine, dextromethorphan, dextromoramide, dezocine, diampromide, diamorphone, dihydrocodeine, dihydromorphine, dimenoxadol, dimepheptanol, dimethylthiambutene, dioaphetylbutyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, loperamide, meperidine (pethidine), meptazinol, metazocine, methadone, metopon, morphine, myrophine, nalbuphine, narceine, nicomorphine, norlevorphanol, normethadone, nalorphine, normorphine, norpinanone, opium, oxycodone, oxymorphone, papaveretum, pentazocine, phenadoxone, phenomorphan, phanazocine, phenoperidine, piminodine, piritramide, prophepzatine, promedol, properidine, propiram, propoxyphene, sulfentanil, tilidine, tramadol, tapentadol, axomadol, faxeladol, or a derivative, prodrug, stereoisomer, and/or salt thereof.

The term "local anesthetic" as used herein has its conventional meaning and here includes but is not limited to amethocaine, articaine, benzocaine, bupivacaine, chloroprocaine, cinchocaine, cocaine, cyclomethycaine, dibucaine, dimethocaine, etidocaine, ethyl aminobenzoate, eugenol, levobupivacaine, lidocaine, menthol, mepivacaine, neosaxitoxin, oxethazaine, oxybuprocaine, piperocaine, prilocaine, propoxycaine, procaine, proparacaine, ropivacaine, saxitoxin, tetracaine, tetrodotoxin, trimecaine, or a derivative, prodrug, stereoisomer, and/or salt thereof.

The term "benzodiazepine" as used herein has its conventional meaning and here includes but is not limited to adinazolam, alprazolam, bentazepam, bretazenil, bromazepam, brotizolam, camazepam, cinazepam, cinolazepam, chlordiazepoxide, climazolam, clobazam, clonazepam, clonazolam, clorazepate, clotiazepam, cloxazolam, delorazepam, diazepam, diclazepam, ethyl carfluzepate, estazolam, etizolam, ethyl loflazepate, flubromazepam, flubromazolam, flunitrazepam, flurazepam, flutazolam, halazepam, ketazolam, loprazolam, lorazepam, lormetazepam, medazepam, mexazolam, midazolam, nifoxipam, nimetazepam, N-desmethyladinazolam, nitrazepam, nordiazepam, oxazepam, phenazepam, pinazepam, prazepam, premazepam, pyrazolam, quazepam, rilmazafone, temazepam, tetrazepam, thienalprazolam, triazolam, or a derivative, prodrug, stereoisomer, and/or salt thereof.

The term "barbiturate" as used herein has its conventional meaning and here includes but is not limited to allobarbital, amobarbital, aprobarbital, alphenal, barbital, barbexaclone, brallobarbital, butabarbital, butalbital, butallylonal, butobarbital, crotylbarbital, cyclobarbital, cyclopal, desoxyphenobarbital, diphenylbarbituric acid, ethallobarbital, febarbamate, heptabarbital, hexethal, hexobarbital, mephobarbital, metharbital, methohexital, methylphenobarbital, narcobarbital, nealbarbital, pentobarbital, phenobarbital, probarbital, propallylonal, proxibarbal, proxibarbital, reposal, secbutabarbital, secobarbital, sigmodal, talbutal, thialbarbital, thiamylal, thiobarbital, thiobutabarbital, thiopental, valofane, vinbarbital, vinylbital, or a derivative, prodrug, stereoisomer, and/or salt thereof.

The term "NMDA-antagonist" as used herein has its conventional meaning and here refers at least to N-methyl-D-aspartate (NMDA) calcium channel antagonist and includes but is not limited to amantadine, aptiganel, caroverine, dextrorphan, dextromethorphan, fullerenes, ibogaine, ketamine, lidocaine, memantine, dizocilpine, neramexane, norketamin, delucemine, 3-fluoro-γ-(3-fluorophenyl)-N-methyl-benzenepropanamine hydrochloride, phencyclidine, tiletamine, remacemide decahydro-6-(phosphonomethyl)-3-isoquinolinecarboxylic acid, (3S,4aR,6S,8aR)-decahydro-6-(phosphonomethyl)-3-isoquinolinecarboxylic acid, (2R,4S)-rel-4-(1H-tetrazol-5-yl-methyl)-2-piperidine carboxylic acid, α-amino-2-(2-phosphonoethyl)-cyclohexanepropanoic acid, glutathione, carbamathione, 5-phosphono-norvaline, 4-(3-phosphonopropyl)-2-piperazine-carboxylic acid, seifotel, cis-4(phono-methyl)-2-piperidine-carboxylic acid, (3E)-2-amino-4-methyl-5-phosphono-3-pentenoic acid, (3E)-2-amino-4-methyl-5-phosphono-3-pentenoic acid, 1-ethyl ester, (αS)-α-amino-2'-chloro-5-(phosphonomethyl)-[1,1'-biphenyl]-3-propanoic acid, S-nitrosoglutathione, camprosate, arcaine, conantokin-G, eliprodil, haloperidol, ifenprodil, traxoprodil, (R,S)-α-(4-hydroxyphenyl)-β-methyl-4-(phenylmethyl)-1-piperidine propanol, aminocyclopropanecarboxylic acid, 7-chlorokynurenic acid, D-cycloserine, gavestinel, 4,6-dichloro-3-[(E)-(2-oxo-1-phenyl-3-pyrrolidinylidene)methyl]-1H-indole-2-carboxylic acid monosodium salt, licostinel, 8-chloro-2,3-dihydropyridazino[4,5-b]quinoline-1,4-dione 5-oxide 2-hydroxy-N,N,N-trimethylethanaminium salt, 7-chloro-4-hydroxy-3-(3-phenoxyphenyl)-2(1H)-quinolinone, 3-amino-1-hydroxy-2-pyrrolidinone, 7-chloro-4-hydroxy-2-(4-methoxy-2-methylphenyl)-1,2,5,10-tetra-hydropyridanizo[4,5-b]quinoline-1,10-dione, or a derivative, prodrug, stereoisomer, and/or salt thereof.

The term "cannabinoid" as used herein has its conventional meaning and here includes but is not limited to cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, dronabinol, anandamide, nabilone, or a derivative, prodrug, stereoisomer, and/or salt thereof.

The term "anti-epileptic compound" as used herein has its conventional meaning and here includes but is not limited to acetazolamide, beclamide, brivaracetam, carbamazepine, divalproex sodium, eslicarbazepine acetate, ethadionelamotrigine, ethosuximide, felbamate, gabapentin, lamotrigine, levetiracetam, mesuximide, methazolamide, oxcarbazepine, paramethadione, phenacemide, pheneturide, phensuximide, potassium bromide, pregabalin, perampanel, primidone, progabide, seletracetam, sodium valproate, sultiame, tiagabine, topiramate, trimethadione, valnoctamide, valpromide, valproic acid, vigabatrin, zonisamide, or a derivative, prodrug, stereoisomer, and/or salt thereof.

BRIEF DESCRIPTION OF THE DRAWINGS

FIG. 1: Example of the amount of cream squeezed from the distal interphalangeal crease to the end of the finger, referred to as the "fingertip unit" (FTU), used as a practical aid for dosing analgesic creams.

DETAILED DESCRIPTION

It is the aim of the current disclosure to provide a solution for the problem of a lack of an effective treatment of neuropathic pain, inflammatory pain, osteoarthritic pain, musculoskeletal pain, pain due to increased muscle tone and muscle spasms, and/or other chronic pain states, which treatment inflicts side-effects to an acceptable low extent.

This disclosure relates to pharmaceutical compositions for topical use wherein the active pharmaceutical ingredient is the co-analgesic phenytoin, or a derivative, prodrug, stereoisomer or salt thereof in combination with at least one other analgesic compound or co-analgesic compound selected from (a) muscle relaxants, (b) tricyclic antidepressants, (c) tetracyclic antidepressants, (d) alpha 2-adrenergic agonists, (e) selective serotonin reuptake inhibitors, (f) serotonin-norepinephrine reuptake inhibitors, (g) non-steroidal anti-inflammatory drugs, (h) opioid receptor agonists, (i) local anesthetics, (j) benzodiazepines, (k) barbiturates, (l) dimethylsulfoxide, (m) NMDA-antagonists, (n) N-acylethanolamide, (o) cannabinoids, and/or (p) anti-epileptic compounds, a derivative, prodrug, stereoisomer, and/or salt thereof, or any combination thereof.

A first aspect of the disclosure is a pharmaceutical composition wherein the active pharmaceutical ingredients consist of:
  a) a first co-analgesic selected from phenytoin or a derivative, a prodrug, a stereoisomer, and/or a salt thereof, or any combination thereof; and
  b) at least one further (co-)analgesic,
and further containing a pharmaceutically acceptable carrier for topical use.

In one embodiment, the pharmaceutical composition of the disclosure is a pharmaceutical topical composition wherein the active pharmaceutical ingredients consist of:
  a) a first co-analgesic selected from phenytoin or a derivative, a prodrug, a stereoisomer, and/or a salt thereof, or any combination thereof; and
  b) at least one further (co-)analgesic,
and further containing a pharmaceutically acceptable carrier for topical use.

The pharmaceutical composition of the disclosure comprises a therapeutic co-analgesic effect booster provided by the booster compound phenytoin, or a derivative, prodrug, stereoisomer, and/or salt thereof, which booster compound is combined with a therapeutically active dose of analgesic compound(s) or co-analgesic compound(s) in a topical pharmaceutical composition. This booster effect is apparent by the observation of: 1) an intensified and synergistic therapeutic effect of the (co-)analgesic compound with the purpose of alleviating neuropathic pain, inflammatory pain, musculoskeletal pain, pain due to muscle spasms, and/or other chronic pain states, 2) a faster onset of pain relieving effect, 3) a longer duration of analgesia, and/or 4) reinstating analgesic effects, when decreasing analgesic effect occurs after repeated use of a topical pharmaceutical composition containing at least one analgesic or co-analgesic compound.

One embodiment of the disclosure is the pharmaceutical composition according to the disclosure, wherein the first co-analgesic of a) is phenytoin, a phenytoin derivative, a phenytoin prodrug, a phenytoin stereoisomer, and/or a salt thereof, or any combination thereof, selected from phenytoin sodium, fosphenytoin, hydroxyphenytoin, 5-(3-hydroxyphenyl)-5-phenylhydantoin, 5-phenyl-5-(4-hydroxyphenyl) hydantoin glucuronide, ropitoin, ropitoin hydrochloride, 5-(2-hydroxyphenyl)-5-phenylhydantoin, 5-(3,4-dihydroxy-1,5-cyclohexadien-1-yl)-5-phenylhydantoin, N-aminodiphenylhydantoin, 5-(3,4-dihydroxyphenyl)-5-phenylhydantoin, PC-796, 5-p-methylphenyl-5-phenylhydantoin, 1-acetyl-3-acetoxy-5',5-diphenylhydantoin, 3-hydroxymethylphenytoin N,N-dimethylglycine ester, 3-(hydroxymethyl)phenytoin N,N-dimethylaminoethyl carbonate, 5-(4-hydroxy-3-methoxyphenyl)-5-phenylhydantoin, 3-pentanoyl-5,5-diphenylhydantoin, 3-(2-propylpentanoyl)-5,5-diphenylhydantoin, 5,5-bis(4-hydroxyphenyl)hydantoin, 3-(hydroxymethyl)phenytoin, phenytoin dihydrodiol, 4-aminophenytoin, N,N-dichlorophenytoin, diphenylthiohydantoin, diphenylhydantoin-3-phenyltricarbonylchromium ethyl acetate, 5,5-diphenylhydantoin-3-valerate-bovine serum albumin, phenytoin-1-methylnicotininate, 2-cyanoguanidinophenytoin, phenytoin-bis-hydroxyisobutyrate, N-acetylphenytoin, diphenylhydantoic acid, N'-3-oxymethylglucuronide phenytoin, diphenylhydantil, 5-(4'-fluorophenyl)-5-phenylhydantoin, azumolene, 5,5-bis(4-trifluoromethylphenyl)hydantoin, 5,5-bis(4-methylphenyl)hydantoin, 5,5-bis(4-methoxyphenyl)hydantoin, 5-(4-methoxyphenyl)-5-phenylhydantoin, and 5-(4-dimethylaminophenyl)-5-phenylhydantoin, and other 5,5-diphenylimidazolidine or a derivative, prodrug, stereoisomer, and/or salt thereof.

One embodiment of the disclosure is the pharmaceutical composition according to the disclosure, wherein the first co-analgesic is phenytoin, phenytoin sodium or a combination thereof.

One embodiment of the disclosure is the pharmaceutical composition according to the disclosure, wherein the at least one further (co-)analgesic of b) is/are selected from a muscle relaxant, a tricyclic antidepressant, a tetracyclic antidepressant, an alpha 2-adrenergic agonist, a selective serotonin reuptake inhibitor, a serotonin-norepinephrine reuptake inhibitor, a serotonin-noradrenalin reuptake inhibitor, a non-steroidal anti-inflammatory drug, an opioid receptor agonist, a local anesthetic, a benzodiazepine, a barbiturate, dimethylsulfoxide, an NMDA-receptor antagonist, an N-acylethanolamide, a cannabinoid, and/or an anti-epileptic compound.

One embodiment of the disclosure is the pharmaceutical composition of the disclosure, wherein the first co-analgesic of a) is phenytoin or phenytoin sodium or the combination thereof, and wherein the at least one further (co-)analgesic of b) is selected from ketamine, baclofen, clonidine, loperamide, lidocaine and isosorbide dinitrate, or wherein the at least one further (co-)analgesics of b) are the combination of baclofen and amitriptyline, or loperamide and amitriptyline, or baclofen and loperamide.

One embodiment of the disclosure is the pharmaceutical composition of the disclosure, wherein the first co-analgesic of a) is phenytoin or phenytoin sodium or the combination thereof, and wherein the at least one further (co-)analgesic of b) is isosorbide dinitrate.

In one embodiment, the pharmaceutical composition according to the disclosure is the pharmaceutical composition, wherein the at least one further (co-)analgesic of b) is/are selected from a muscle relaxant, a tricyclic antidepressant, a tetracyclic antidepressant, an alpha 2-adrenergic agonist, a selective serotonin reuptake inhibitor, a serotonin-norepinephrine reuptake inhibitor, a serotonin-noradrenalin reuptake inhibitor, a non-steroidal anti-inflammatory drug, an opioid receptor agonist, a benzodiazepine, a barbiturate, dimethylsulfoxide, an N-acylethanolamide, a cannabinoid, and/or an anti-epileptic compound.

In one embodiment, the pharmaceutical composition according to the disclosure is the pharmaceutical composition, wherein the first co-analgesic of a) is phenytoin or phenytoin sodium or the combination thereof, and wherein the at least one further (co-)analgesic of b) is selected from baclofen, clonidine, loperamide and isosorbide dinitrate, or wherein the at least one further (co-)analgesics of b) are the combination of baclofen and amitriptyline, or loperamide and amitriptyline, or lidocaine and isosorbide dinitrate, or baclofen and loperamide.

One embodiment of the disclosure is the pharmaceutical composition according to the disclosure, wherein the topical pharmaceutical composition contains phenytoin, in an amount between approximately 0.5% and approximately 20% by weight of the topical cream, preferably between about 5% and about 20% by weight of the topical cream, such as about 5%, about 10%, about 15% and about 20% by weight of the topical cream.

One embodiment of the disclosure is the pharmaceutical composition according to the disclosure, wherein the pharmaceutically acceptable carrier for topical use is a cream.

It was desired to solve, amongst others, the problem of the treatment of pain raising in and around the sensory afferents in the skin, that is to say, pain related to peripheral neurogenic inflammation, in and around the sensory afferents in the skin, the nociceptors and the tissue around these afferents, where pathogenetic pathways can be located in the epidermal part of the skin. It was surprisingly found that topically administered phenytoin indeed reduces peripheral neuropathic pain in a cream formulation, without giving rise to systemic side effects, as the topically applied phenytoin did not penetrate the blood, and no blood levels for phenytoin could be detected. Of course, it is appreciated by the skilled person that also parts of such pathogenic pathways related to pain in and around the sensory afferents in the skin, can be located in the epidermal part of the skin. The phenytoin formulation disclosed herein did not reach detectable concentrations of phenytoin in the plasma of patients treated with a pharmaceutical composition, as measured in 16 patients after application of phenytoin 10% cream. Even in one patient after application of 6.7 grams of phenytoin 10% cream (670 mg phenytoin), once daily during 25 days, and blood sampling 2.5 hours after last application, no detectable phenytoin in plasma was measured. This absence of the active pharmaceutical ingredient phenytoin in blood is in clear contrast with other topical analgesic formulations, such as formulations containing the analgesic diclofenac epolamine (180 mg) in a 1.3% patch, lidocaine, amitriptyline, ketamine and doxepin cream.

The topical formulation of diclofenac epolamine 1.3% patch, for instance, is designed to reach active drug levels in the muscles. Application of the patch on human skin and on pig skin resulted in measurable therapeutic plasma levels (mean peak concentration of about 1.8 ng/mL, and maximal measured concentration of about 6.1 ng/mL) [Petersen & Rovati, 2009; Tse S. et al., 2012]. This diclofenac epolamine 1.3% formulation reached comparable concentrations of diclofenac in muscles beneath the patch application site to corresponding tissue levels after oral administration (Cmax. values of 879 ng/mL after topical administration and 1160 ng/mL after oral administration) [Tse S. et al., 2012]. Also doxepin 5% cream showed a plasma concentration of doxepin of maximal 47 ng/ml, with a mean of 10.8 ng/ml in 19 patients [Keskin G. et al., 1999]. The same holds true for a great number of other analgesics [Glinn M A. et al., 2017].

One embodiment of the disclosure is the pharmaceutical composition according to the disclosure, wherein the at least one further (co-)analgesic is a muscle relaxant, preferably baclofen, preferably at an amount of between approximately 0.5% and approximately 20% by weight of the topical cream.

One embodiment of the disclosure is the pharmaceutical composition according to the disclosure, wherein the at least one further (co-)analgesic is a tricyclic antidepressant, preferably amitriptyline, preferably at an amount of between approximately 0.5% and approximately 20% by weight of the topical cream.

One embodiment of the disclosure is the pharmaceutical composition according to the disclosure, wherein the at least one further (co-)analgesic is a tetracyclic antidepressant, preferably mianserin, preferably at an amount of between approximately 0.5% and approximately 20% by weight of the topical cream.

One embodiment of the disclosure is the pharmaceutical composition according to the disclosure, wherein the at least one further (co-)analgesic is an alpha 2-adrenergic agonist, preferably clonidine, preferably at an amount of between approximately 0.1% and approximately 20% by weight of the topical cream.

One embodiment of the disclosure is the pharmaceutical composition according to the disclosure, wherein the at least one further (co-)analgesic is a selective serotonin reuptake inhibitor, preferably paroxetine, preferably at an amount of between approximately 0.5% and approximately 20% by weight of the topical cream.

One embodiment of the disclosure is the pharmaceutical composition according to the disclosure, wherein the at least one further (co-)analgesic is a serotonin-norepinephrine reuptake inhibitor, preferably venlafaxine, preferably at an amount of between approximately 0.5% and approximately 20% by weight of the topical cream.

One embodiment of the disclosure is the pharmaceutical composition according to the disclosure, wherein the at least one further (co-)analgesic is a non-steroidal anti-inflammatory drug, preferably diclofenac, preferably at an amount of between approximately 0.5% and approximately 20% by weight of the topical cream.

One embodiment of the disclosure is the pharmaceutical composition according to the disclosure, wherein the at least one further (co-)analgesic is an opioid receptor agonist, preferably loperamide, preferably at an amount of between approximately 0.1% and approximately 20% by weight of the topical cream.

One embodiment of the disclosure is the pharmaceutical composition according to the disclosure, wherein the at least one further (co-)analgesic is a local anesthetic lidocaine, preferably at an amount of between approximately 0.5% and approximately 20% by weight of the topical cream.

One embodiment of the disclosure is the pharmaceutical composition according to the disclosure, wherein the at least one further (co-)analgesic is a benzodiazepine, preferably diazepam, preferably at an amount of between approximately 0.5% and approximately 20% by weight of the topical cream.

One embodiment of the disclosure is the pharmaceutical composition according to the disclosure, wherein the at least one further (co-)analgesic is a barbiturate, preferably secobarbital, preferably at an amount of between approximately 0.5% and approximately 20% by weight of the topical cream.

One embodiment of the disclosure is the pharmaceutical composition according to the disclosure, wherein the at least one further (co-)analgesic is dimethylsulfoxide, preferably at an amount of between approximately 10% and approximately 80% by weight of the topical cream.

One embodiment of the disclosure is the pharmaceutical composition according to the disclosure, wherein the at least one further (co-)analgesic is an NMDA-antagonist, preferably (l, r or racemic) ketamine, preferably at an amount of between approximately 0.5% and approximately 20% by weight of the topical cream.

One embodiment of the disclosure is the pharmaceutical composition according to the disclosure, wherein the at least one further (co-)analgesic is a cannabinoid, preferably cannabidiol, preferably at an amount of between approximately 0.5% and approximately 20% by weight of the topical cream.

One embodiment of the disclosure is the pharmaceutical composition according to the disclosure, wherein the at least one further (co-)analgesic is an anti-epileptic compound, preferably pregabalin, preferably at an amount of between approximately 0.5% and approximately 20% by weight of the topical cream.

One embodiment of the disclosure is the pharmaceutical composition according to the disclosure, wherein the at least one further (co-)analgesic of b) is/are selected from a muscle relaxant, a tricyclic antidepressant, a tetracyclic antidepressant, an alpha 2-adrenergic agonist, a selective serotonin reuptake inhibitor, a serotonin-norepinephrine reuptake inhibitor, a serotonin-noradrenalin reuptake inhibitor, a non-steroidal anti-inflammatory drug, an opioid receptor agonist, a local anesthetic, a benzodiazepine, a barbiturate, dimethylsulfoxide, an NMDA-receptor antagonist, an N-acylethanolamide, a cannabinoid, and/or an anti-epileptic compound.

One embodiment of the disclosure is the pharmaceutical composition for use in the treatment of chronic pain according to the disclosure, wherein the composition contains between approximately 0.5% and approximately 20% phenytoin by weight of the cream, and wherein the composition is administered every other day, daily, twice daily, three times daily or four times daily for a period of at least one day, at least one week, at least one year, or longer. One embodiment of the disclosure is the pharmaceutical composition for use in the treatment of chronic pain according to the disclosure, wherein the composition contains between approximately 0.5% and approximately 30% phenytoin by weight of the cream, and wherein the composition is administered every other day, daily, twice daily, three times daily or four times daily for a period of at least one day, at least one week, at least one year, or longer. This way, a continuous decrease of (peripheral) neuropathic pain, inflammatory pain, musculoskeletal pain, pain due to muscle spasms, and/or other chronic pain states is achieved upon administering the pharmaceutical composition of the disclosure to a patient suffering from chronic pain.

In one embodiment, the pharmaceutical composition for use in the treatment of chronic pain according to the disclosure, is a pharmaceutical topical composition wherein the use is the topical use in the treatment of chronic pain according to the disclosure.

In one embodiment, the pharmaceutical composition for use in the treatment of chronic pain according to the disclosure, is a pharmaceutical topical composition wherein the use is the topical use on intact skin of the treated person in the treatment of chronic pain according to the disclosure.

In one embodiment, the pharmaceutical composition for use in the treatment of chronic pain according to the disclosure, is a pharmaceutical topical composition wherein the use is the topical use on healthy intact skin of the treated person in the treatment of chronic pain according to the disclosure. Here, intact skin and healthy intact skin have their common scientific meaning and here refer to non-injured skin free of e.g., ulcers, wounds, lesions, cuts, and refer to skin comprising a closed outer layer of epidermis.

Topical Pharmaceutical Compositions

The topical formulations of the disclosure herein are pharmaceutical compositions proposed for topical administration on the skin and mucosa (e.g., buccal, vaginal and rectal). Examples of topical pharmaceutical compositions are creams, gels, dispersions, emulsions, foams, mists, mouth washes, lotions, salves, ointments, sprays, aerosols, plasters, oils, and suspensions. Preferably, the topical pharmaceutical composition of the disclosure is a cream.

One embodiment of the disclosure is the pharmaceutical composition according to the disclosure, wherein the pharmaceutically acceptable carrier for topical use is a cream, a gel, a dispersion, an emulsion, a foam, a mist, a mouth wash, a lotion, a salve, an ointment, an oil, a spray, an aerosol, a suppository, a suspension, a plaster, a passive or active topical device for absorption through the skin and mucous membrane.

One embodiment of the disclosure is the pharmaceutical composition according to the disclosure, wherein the pharmaceutically acceptable carrier for topical use is a cream.

One embodiment of the disclosure is the pharmaceutical composition according to the disclosure, wherein the pharmaceutically acceptable carrier for topical use comprises at least one skin penetration enhancer, preferably selected from macrogol cetostearyl ether, cetostearyl alcohol, decylis oleas or any combination thereof.

Without wishing to be bound by theory, phenytoin, phenytoin sodium and their derivatives, prodrugs, stereoisomers and further salts thereof, and, in particular, phenytoin and phenytoin sodium, have properties particularly suitable for penetration of the skin, such as human skin, such as intact skin. That is to say, it is common general knowledge that molecules smaller than 500 Dalton can penetrate the stratum corneum of the skin. The stratum corneum barrier will allow the penetration of lipid soluble molecules more readily than water-soluble compounds. Water-soluble molecules may penetrate through an alternative way, the openings of sweat glands and hair follicles [Bos et al.]. Active pharmaceutical ingredients (APIs) used in the described pharmaceutical formulations of the disclosure have a molecular weight smaller than 500 Dalton. Therefore, without wishing to be bound by theory, skin penetration enhancers are not required for these APIs in order to be able to penetrate the stratum corneum of the skin to reach the nerve endings present in the next skin layer, the stratum granulosum. Since it was found that phenytoin sodium in cream, which is more hydrophilic than phenytoin, has the same therapeutic effect as phenytoin cream, lipophilicity and hydrophilicity of these compounds is not a limiting factor for these molecules smaller than 500 Dalton with regard to their ability to penetrate the (human) skin.

Penetration strategies seem not to be relevant in general for molecules with a positive log P (partition coefficient between octanol and water) and for molecules smaller than 500 Dalton [Korinth et al., Bos et al.]. For example, Amitriptyline HCL 10% water solution (in total 2 mg amitriptyline) topically applied on the skin of mice resulted in effective transdermal absorption with in the lungs the highest detection of amitriptyline [Baily]. Another example: the cumulative percentage of permeated lidocaine comparing to penetration enhancement techniques (lidocaine into nanostructured lipid carriers or nanoethosomes) with control (hydroalcoholic lidocaine solution) did not reach statistical significance [Babaei et al.]. In Table 11, below, an overview of a series of exemplifying compounds is provided, the compounds known for their ability to penetrate the skin.

Indeed, referring to Case aa, bb, cc and dd, below, it is clear that a pharmaceutical composition comprising phenytoin, either further comprising one or more skin penetration enhancers, or not comprising a skin penetration enhancer, are comparably efficient and efficacious in providing relief from peripheral neuropathic pain in patients after topical administration of the pharmaceutical composition comprising phenytoin on the skin of the human patient.

Thus, the pharmaceutical composition of the disclosure may or may not comprise one or more skin penetration enhancers, according to the disclosure. Including one or more skin penetration enhancers in the pharmaceutical composition of the disclosure may have a beneficial effect on the time to onset of the pain relieving effect of the analgesics, and may support the penetration of the analgesics through the skin, once the pharmaceutical composition for topical use on the skin is administered onto the skin of a patient, preferably a human patient, according to the disclosure.

Topical Pharmaceutical Compositions of the Disclosure

The cream base used for any of the topical creams of the disclosure described above is any pharmaceutically acceptable carrier that is capable of dermal delivery of the active pharmaceutical ingredients contained in the pharmaceutical composition of the disclosure, i.e., the first co-analgesic compound and the at least one further (co-)analgesic compound. By way of example, the cream base is a cream, gel, dispersion, emulsion, foam, mist, mouth wash, lotion, salve, ointment, oil, spray, aerosol, suppository, suspension, plaster and various passive and active topical devices for absorption through the skin and mucous membranes, according to the disclosure. Typical pharmaceutically acceptable carriers according to the disclosure are, for example, water, mixtures of water and water-miscible solvents such as lower alkanols or vegetable oils. An oil-in-water emulsion providing a cream base is most preferred for general applications on the skin, according to the disclosure. A liquid such as a suspension or emulsion is desirable for treating the scalp. A typical cream for topical application that can be used according to the methods and compositions of the disclosure herein include a mixture of water, glycerin, propylene glycol, and methylparaben. The base of the disclosure preferably also includes other conventional emulsifiers and emollients including alginates, glyceryl stearate, PEG-100 stearate, cetyl alcohol, propylparaben, butylparaben, sorbitols, polyethoxylated anhydrosorbitol monostearate, white petrolatum, triethanolamine, lanolin, cocoa butter, shea butter and the like, according to the disclosure.

A second aspect of the disclosure is a method for preparing a pharmaceutical composition for use in the treatment of chronic pain according to the disclosure, comprising the steps of:
a. providing oil-soluble constituents and separately providing water soluble constituents of a pharmaceutically acceptable carrier for topical use;
b. providing a first co-analgesic selected from phenytoin or a derivative, a prodrug, a stereoisomer, and/or a salt thereof, preferably phenytoin or phenytoin sodium or a combination thereof, and providing at least one further (co-)analgesic;
c. mixing the oil-soluble constituents at between 20° C. to 95° C. of step a. by stirring, and separately, dissolving the water-soluble constituents of step a. in water, wherein the water is optionally heated to between 20° C. to 95° C. while dissolving the water-soluble constituents of step a., thereby providing an aqueous solution;
d. combining the mixed oil-soluble constituents of step c. with the aqueous solution of step c., wherein the temperature of the mixed oil-soluble constituents and the aqueous solution is about the same, preferably about 70° C., and mixing by stirring, thereby providing the pharmaceutically acceptable carrier for topical use;
e. mixing the (co-)analgesics of step b. with the pharmaceutically acceptable carrier of step d. by adding the (co-)analgesics of step b. to the carrier while stirring for between 5 to 20 minutes, preferably for about 10 minutes, wherein the temperature of the (co-)analgesics and of the pharmaceutically acceptable carrier is preferably room temperature, preferably about 20° C. while mixing; and
f. optionally adjusting the pH of the pharmaceutical composition to between 4.0 and 6.5.

In one embodiment, the method for preparing a pharmaceutical composition for use in the treatment of chronic pain according to the disclosure is the method, wherein the pharmaceutically acceptable carrier for topical use of step d. is a cream for epidermal delivery of phenytoin or a derivative, a prodrug, a stereoisomer, and/or a salt thereof, preferably phenytoin or phenytoin sodium or a combination thereof of step b.

In one embodiment, the method for preparing a pharmaceutical composition for use in the treatment of chronic pain according to the disclosure is a method for preparing a pharmaceutical topical composition for use in the treatment of chronic pain according to the disclosure.

A third aspect of the disclosure is a pharmaceutical composition according to the disclosure or provided by the method of the disclosure, for use in the treatment of chronic pain according to the disclosure.

One embodiment of the disclosure is a pharmaceutical composition according to the disclosure or provided by the method of the disclosure, for use in the treatment of chronic pain according to the disclosure, wherein the chronic pain is neuropathic pain, peripheral neuropathic pain, inflammatory pain, musculoskeletal pain, pain due to muscle spasms, pain due to increased muscle tone, osteoarthritic pain, muscular headache, tension-type headache, migraine, cluster headache, atypical facial pain, referred pain, vulvodynia, proctodynia, or combinations thereof.

In one embodiment, the pharmaceutical composition for use in the treatment of chronic pain according to the disclosure is the pharmaceutical composition, wherein the chronic pain is peripheral neuropathic pain.

In one embodiment, the pharmaceutical composition according to the disclosure or provided by the method of the disclosure for use in the treatment of chronic pain, is the pharmaceutical composition wherein the at least one further (co-)analgesic is lidocaine and wherein the chronic pain is one or more selected from the list consisting of peripheral neuropathic pain and vulvodynia, or wherein the chronic pain is one or more selected from the list consisting of pain in the area of intact skin and pain in the area of mucosa.

In one embodiment, the pharmaceutical composition for use according to the disclosure is the pharmaceutical composition, wherein the first co-analgesic is phenytoin, phenytoin sodium or a combination thereof, and wherein the pharmaceutical composition is topically administered, and wherein the first co-analgesic is delivered epidermally.

In one embodiment, the pharmaceutical composition for use according to the disclosure is the pharmaceutical composition, wherein the at least one further (co-)analgesic is selected from ketamine, baclofen, clonidine, loperamide, lidocaine and isosorbide dinitrate, or wherein the at least one further (co-)analgesics are the combination of baclofen and amitriptyline, or loperamide and amitriptyline, or baclofen and loperamide.

One embodiment of the disclosure is a pharmaceutical composition according to the disclosure or provided by the method of the disclosure, for use in the treatment of chronic pain according to the disclosure, wherein the chronic pain is neuropathic pain selected from peripheral neuropathy caused by diabetes type 1 or 2, or induced by a noxious substance such as alcohol, due to vitamin B1, B6 and/or B12 deficiency, hypervitaminosis B6, hypothyroidism, chemotherapeutic compound such as paclitaxel or a taxane derivative, vincristine or a vinca alkaloid, cisplatin or a platinum derivate, drug-induced neuropathy, a compound for the treatment of infectious disease such as streptomycin, didanosine or zalcitabine, a chemically toxic compound, trigeminal neuralgia, post-herpetic neuralgia, intercostal neuralgia, entrapment neuropathy such as carpal tunnel syndrome, tarsal tunnel syndrome, abdominal cutaneous nerve entrapment syndrome, sciatic pain chronic idiopathic sensory neuropathy, small fiber neuropathy, hereditary motor and sensory neuropathies, chronic inflammatory demyelinating polyneuropathy, infectious disease conditions such as post-polio syndrome, AIDS or HIV-associated, Lyme-associated, Sjögren-associated, lymphomatous neuropathy, myelomatous neuropathy, carcinomatous neuropathy, acute pan autonomic neuropathy, vasculitic/ischaemic neuropathy and a mono- and polyneuropathy, complex regional pain syndrome type I and II (reflex sympathetic dystrophy), central neuropathic pain such as thalamic neuropathy, spinal cord injury neuropathy, post stroke pain, multiple sclerosis neuropathy, syringomyelia, a spinal cord tumor, phantom limb pain, restless genital syndrome with pain, post-surgical scar pain including scar pain after cardiac surgery and mastectomy.

One embodiment of the disclosure is a pharmaceutical composition according to the disclosure or provided by the method of the disclosure, for use in the treatment of chronic pain according to the disclosure, wherein the dosing frequency of the pharmaceutical composition is between once every other day and eight times daily, preferably six, five, four, three, two or one times daily.

It was found that when a topical pharmaceutical composition of the disclosure is administered at a dose every other day, daily, twice daily, three times daily or four times daily for a period of at least one day, at least one week, at least one year, or longer, e.g., chronically, during the lifespan of the patient, a continuous decrease is achieved of (peripheral) neuropathic pain, inflammatory pain, musculoskeletal pain, pain due to muscle spasms, and/or other chronic pain states. The amount of administered topical pharmaceutical composition of the disclosure is preferably between 0.1 grams to 4 grams per application. The "fingertip unit" (FTU) is a practical and preferred aid for dosing analgesic creams of the disclosure. A FTU is the amount of cream squeezed from the distal interphalangeal crease to the end of the finger (see FIG. 1). A streak cream from a tube with an opening with a diameter of 6 mm is approximately 0.6 g; a streak cream from a tube with an opening with a diameter of 5 mm is approximately 0.5. For one foot of an adult, about 0.8 FTU cream is required and for one hand, about 0.5 FTU cream is required. As part of the disclosure a more flexible dosing is also possible on the skin because since reaching any detectable systemic concentrations of the active pharmaceutical ingredients in the pharmaceutical composition of the disclosure is not aimed at.

Patients are instructed to apply 3 to 5 times daily with a maximum 2 FTUs per application of the pharmaceutical composition of the disclosure, unless side effects might appear, if at all. In case side effects appear (not observed in the exemplary cases, provided in the Examples section, below), patients are instructed not to apply any cream on the neuropathic pain area until the side effects disappear. Thereafter patients are instructed to apply half of the dose to prevent side effects and apply less frequently the cream. As said before, administering the topical pharmaceutical composition of the disclosure to patients suffering from chronic pain according to the disclosure has not resulted in any reported adverse events or side effects. When needed patients may apply the topical pharmaceutical composition of the disclosure more than 3 times a day, up to 8 times a day. If the pain was still not managed, the dose is increased with 2 to 4 FTUs per application, according to the disclosure.

One embodiment of the disclosure is the pharmaceutical composition for use in the treatment of chronic pain according to the disclosure, wherein the pharmaceutical composition is administered during a period of at least one day, preferably at least one week, more preferably at least one month, most preferably at least one year, preferably the pharmaceutical composition is administered for one to ten years, more preferably the pharmaceutical composition is administered chronically. It is to be understood that it is part of the disclosure that the pharmaceutical composition for use in the treatment of chronic pain according to the disclosure is administered to patients suffering from chronic pain for the rest of their lifespan. This way, the chronic pain is at least less intense and preferably patients are relieved from the chronic pain to a large extent or even completely.

Phenytoin as a Co-Analgesic Effect Booster for Analgesic and Co-Analgesic Compounds in a Pharmaceutical Composition of the Disclosure The therapeutic co-analgesic effect booster of the disclosure is provided by at least one active compound that is phenytoin, or a derivative, prodrug, stereoisomer, and/or salt thereof, which active compound is added to a therapeutically active analgesic of co-analgesic compound in a topical pharmaceutical composition, the combination of the active compound and the therapeutically active analgesic of co-analgesic compound providing for an intensifying therapeutic effect of the active compound in the topical pharmaceutical composition, faster onset of pain relieving effect, longer duration of analgesia and/or reinstating analgesic effects when decreasing analgesic effect occurs after repeated use.

One embodiment of the disclosure is the pharmaceutical composition according to the disclosure, wherein the composition comprises phenytoin sodium and wherein the composition is a topical formulation further containing as the at least one further (co-)analgesic selected from amitriptyline HCl, baclofen, diclofenac, loperamide, clonidine HCl, lidocaine, ketamine, isosorbide dinitrate, or other analgesics, or any combination thereof. The pharmaceutical composition according to the disclosure surprisingly shortened the time of onset of therapeutic effect achieved with the at least one further (co-)analgesic, enhanced the analgesic effect and prolonged its duration in patients with pain, and more specifically neuropathic pain. Furthermore, surprisingly it was found that a pharmaceutical composition of the disclosure comprising phenytoin (sodium) as an effect booster had a shortened therapeutic onset of effect of phenytoin cream of between 5 minutes and 15 minutes, while the duration of therapeutic effect is prolonged up to between 3 hour and 24 hours, with a mean time of 10 hours. Without the presence of phenytoin sodium in the pharmaceutical composition, the therapeutic onset was between 20 and 30 minutes and the duration of the therapeutic effect was about 2 to 6 hours. See, for example, the cases 2, 3, 4, 8 and 9 in the Example section below, where it is shown that patients who suffered from chronic pain were treated with the pharmaceutical composition of the disclosure and reported an onset of the pain relieving effect of the composition already as fast as within 5 minutes or even within 3 minutes, according to the disclosure.

Surprisingly, it was found that the combination of phenytoin 5% with amitriptyline 10% cream showed superiority over 5% phenytoin with ketamine 10% cream (see also Case 11 and Case 12 in the Examples section, below, for more detail), and in addition it was also found that the combination of phenytoin 5% with amitriptyline 10% cream showed superiority over lidocaine 3% cream with or without phenytoin 5%. Based on the analyses of all outcomes of treatments of patients with creams of the disclosure, the order of effectiveness of combination creams of the disclosure, ranked from high to low with regard to effectiveness of treatment when relief from pain is assessed, is as follows: 1) phenytoin/amitriptyline, 2) phenytoin/baclofen, 3) phenytoin/clonidine, 4) phenytoin/isosorbide dinitrate 5) phenytoin/loperamide, 6) phenytoin/ketamine, 7) phenytoin/lidocaine.

The onset of action of the pharmaceutical compositions of the disclosure is surprisingly very fast, within 3 to 30 minutes, and most often within 5 minutes, at least excluding an analgesic effect of the phenytoin via the blood, and making an epidermal mechanism of action for the pharmaceutical compositions of the disclosure highly plausible. It is common general knowledge that after oral administration of an active pharmaceutical ingredient (API), peak plasma concentrations are reached only after 4 to 12 hours [L. Lund et al., 1974].

It is well known to the specialist in the field that APIs delivered orally are leading to values for C.max quicker in time compared to delivery of the same API via topical formulations. The above context clearly supports the topical intra-epidermal mechanism of action of at least the topically administered phenytoin on the skin of a patient, preferably a human patient.

As said before, several topical pharmaceutical compositions for use in the treatment of musculoskeletal pain have been disclosed, previously. For example, U.S. Pat. No.

9,012,402 discloses a topical analgesic pharmaceutical compositions with ketoprofen, a skin penetration enhancer, a thickening agent and a base to adjust pH to provide relief of inflammation and pain in rheumatoid arthritis, osteoarthritis, soft tissue injuries. In U.S. Pat. No. 8,470,886 a topical formulation comprising ibuprofen in a hydro-alcoholic-based solvent system containing tri-ethyl acetate and a surfactant is disclosed. None of these above disclosures, however, mentioned a clinical relevant prolonging analgesic effect when adding an anticonvulsant, especially phenytoin, to another analgesic compound. Such a clinical relevant prolonging analgesic effect when adding an anticonvulsant, especially phenytoin, to another analgesic compound has now surprisingly been found as disclosed herein. Moreover, none of the above disclosures, however, refers to the reinstating effect of adding any active pharmaceutical agent on top of another analgesic compound. Such a reinstating effect of adding any active pharmaceutical agent on top of another analgesic compound, e.g., the addition of phenytoin or phenytoin sodium to any one or more of a (co-)analgesic selected from a muscle relaxant, a tricyclic antidepressant, a tetracyclic antidepressant, an alpha 2-adrenergic agonist, a selective serotonin reuptake inhibitor, a serotonin-norepinephrine reuptake inhibitor, a serotonin-noradrenalin reuptake inhibitor, a non-steroidal anti-inflammatory drug, an opioid receptor agonist, a local anesthetic, a benzodiazepine, a barbiturate, dimethylsulfoxide, an NMDA-receptor antagonist, an N-acylethanolamide, a cannabinoid, and/or an anti-epileptic compound, wherein, for example, the (co-)analgesic is selected from ketamine, baclofen, clonidine, loperamide, lidocaine and isosorbide dinitrate, or wherein the at least one further (co-)analgesics are the combination of baclofen and amitriptyline, or loperamide and amitriptyline, or baclofen and loperamide, has now surprisingly been found and is disclosed herein.

One embodiment of the disclosure is the pharmaceutical composition according to the disclosure, wherein the composition contains 0.1%-30% phenytoin (sodium), preferably 0.1%, 1%, 2%, 4%, 5%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% or any amount in between two indicated amounts, by weight of the composition. One embodiment of the disclosure is the pharmaceutical composition according to the disclosure, wherein the composition contains 0.1%-20% phenytoin (sodium), preferably 0.1%, 1%, 2%, 4%, 5%, 7%, 8%, 9%, 10%, 11%, 12%, 13%, 14%, 15%, 16%, 17%, 18%, 19%, 20% or any amount in between two indicated amounts, by weight of the composition.

In one embodiment, the pharmaceutical composition for use in the treatment of chronic pain according to the disclosure comprises as the first co-analgesic 5% phenytoin by weight of the composition and comprises as the second (co-)analgesic 10% amitriptyline by weight of the composition. Treatment of a patient suffering from chronic pain prolonged the duration of the analgesic effect substantially, which duration of the pain-killing effect was even about tripled when the amount of phenytoin was raised to 10% by weight of the composition. In contrast, for example, in the prior art, an increase of the content of ketamine from 15% to 30% in a composition, while the content of gabapentin was kept at 6% in the composition, did not result in an improved analgesic effect obtainable with this composition, i.e., the duration of the pain relief remained unaltered under influence of doubling the concentration of ketamine in the composition of the prior art.

In one embodiment, the pharmaceutical composition for use in the treatment of chronic pain according to the disclosure comprises as the first co-analgesic phenytoin and comprises as the second (co-)analgesic lidocaine.

In one embodiment, the pharmaceutical composition for use in the treatment of chronic pain according to the disclosure comprises as the first co-analgesic phenytoin and comprises as the second (co-)analgesic lidocaine, wherein the use is in a method for treatment of peripheral neuropathic pain and/or vulvodynia.

In one embodiment, the pharmaceutical composition for use in the treatment of chronic pain according to the disclosure comprises as the first co-analgesic phenytoin and comprises as the second (co-)analgesic lidocaine, wherein the use is in a method for treatment of pain, the pain being localized in the area of intact skin and/or intact mucosa.

According to the disclosure, for the relief of pain in a subject, preferably chronic pain, the topical pharmaceutical composition of the disclosure preferably comprises at least one muscle relaxant, such as baclofen, in an amount between approximately 0.5% and approximately 20% of the topical cream by weight together with a therapeutic effect booster phenytoin (e.g., phenytoin sodium) in an amount between approximately 0.5% and approximately 20% of the topical cream by weight or in an amount between approximately 0.5% and approximately 30% of the topical cream by weight. More preferably, the topical pharmaceutical composition of the disclosure contains baclofen at approximately 5% of the topical cream by weight, and phenytoin sodium, preferably phenytoin approximately 5% of the topical cream by weight.

One embodiment of the disclosure is the pharmaceutical composition for use in the treatment of chronic pain according to the disclosure, wherein the first co-analgesic is between 0.5% to 30% phenytoin and/or phenytoin sodium. One embodiment of the disclosure is the pharmaceutical composition for use in the treatment of chronic pain according to the disclosure, wherein the first co-analgesic is between 0.5% to 20% phenytoin and/or phenytoin sodium, preferably between 5% and 10%, and wherein the at least one further (co-)analgesic is selected from about 10% ketamine, about 5% baclofen, about 0.2% clonidine, about 5% loperamide, about 5% lidocaine and about 0.4% isosorbide dinitrate, or wherein the at least one further (co-)analgesics are the combination of about 5% baclofen and about 5% amitriptyline, or ketamine 10% and amitriptyline 5%, or loperamide 5% and baclofen 5% by weight of the pharmaceutical composition.

In one embodiment, the pharmaceutical composition for use in the treatment of chronic pain according to the disclosure is the pharmaceutical composition, wherein the first co-analgesic is between 5% and 10% phenytoin and/or phenytoin sodium by weight of the pharmaceutical composition, and wherein the at least one further (co-)analgesic is selected from about 10% ketamine by weight of the pharmaceutical composition, about 5% baclofen by weight of the pharmaceutical composition, about 0.2% clonidine by weight of the pharmaceutical composition, about 5% loperamide by weight of the pharmaceutical composition, about 5% lidocaine by weight of the pharmaceutical composition and about 0.4% isosorbide dinitrate by weight of the pharmaceutical composition, or wherein the at least one further (co-)analgesics are the combination of about 5% baclofen and about 5% amitriptyline by weight of the pharmaceutical composition, or ketamine 10% and amitriptyline 5% by weight of the pharmaceutical composition, or loperamide 5% and baclofen 5% by weight of the pharmaceutical composition.

In one embodiment, the pharmaceutical composition for use in the treatment of chronic pain according to the disclosure is the pharmaceutical composition, wherein the first co-analgesic is between 0.5% to 30% phenytoin and/or phenytoin sodium by weight of the pharmaceutical composition or is between 0.5% to 20% phenytoin and/or phenytoin sodium by weight of the pharmaceutical composition, preferably between 5% and 20% by weight of the pharmaceutical composition, more preferably an amount selected from 5%, 10% and 20% by weight of the pharmaceutical composition, and wherein the at least one further (co-) analgesic is selected from about 5% baclofen by weight of the pharmaceutical composition, about 0.2% clonidine by weight of the pharmaceutical composition, about 5% loperamide by weight of the pharmaceutical composition and about 0.4% isosorbide dinitrate by weight of the pharmaceutical composition, or wherein the at least one further (co-)analgesics are the combination of about 5% baclofen and about 5% amitriptyline by weight of the pharmaceutical composition, or ketamine 10% and amitriptyline 5% by weight of the pharmaceutical composition, or loperamide 5% and baclofen 5% by weight of the pharmaceutical composition.

In one embodiment, the pharmaceutical composition for use in the treatment of chronic pain according to the disclosure is the pharmaceutical composition, wherein the first co-analgesic is between 0.5% to 30% phenytoin and/or phenytoin sodium by weight of the pharmaceutical composition, or is between 0.5% to 20% phenytoin and/or phenytoin sodium by weight of the pharmaceutical composition, preferably between 5% and 20% by weight of the pharmaceutical composition, more preferably an amount selected from 5%, 10% and 20% by weight of the pharmaceutical composition, and wherein the at least one further (co-) analgesic is selected from about 5% baclofen by weight of the pharmaceutical composition, about 0.2% clonidine by weight of the pharmaceutical composition, about 5% loperamide by weight of the pharmaceutical composition and about 0.4% isosorbide dinitrate by weight of the pharmaceutical composition, or wherein the at least one further (co-)analgesics are the combination of about 5% baclofen and about 5% amitriptyline by weight of the pharmaceutical composition, or loperamide 5% and baclofen 5% by weight of the pharmaceutical composition.

According to the disclosure, for the relief of pain in a subject the topical pharmaceutical composition of the disclosure preferably comprises at least one tricyclic antidepressant, such as amitriptyline, in an amount between approximately 0.5% and approximately 20% of the topical cream by weight together with a therapeutic effect booster phenytoin (e.g., phenytoin sodium) in an amount between approximately 0.5% and approximately 20% of the topical cream by weight. More preferably, the topical pharmaceutical composition of the disclosure contains amitriptyline at approximately 10% of the topical cream by weight, and phenytoin sodium at approximately 10% of the topical cream by weight.

According to the disclosure, for the relief of pain in a subject the topical pharmaceutical composition of the disclosure comprises at least one tetracyclic antidepressant, such as mianserin, in an amount of between approximately 0.5% and approximately 20% of the topical cream by weight together with a therapeutic effect booster phenytoin (e.g., phenytoin sodium) in an amount of between approximately 0.5% and approximately 20% of the topical cream by weight. More preferably, the topical pharmaceutical composition of the disclosure contains mianserin at approximately 10% of the topical cream by weight, and phenytoin sodium at approximately 10% of the topical cream by weight, preferably phenytoin at approximately 10% of the topical cream by weight.

According to the disclosure, for the relief of pain in a subject the topical pharmaceutical composition of the disclosure comprises at least one alpha 2-adrenergic agonist, such as clonidine, in an amount of between approximately 0.1% and approximately 20% of the topical cream by weight together with a therapeutic effect booster phenytoin (e.g., phenytoin sodium) in an amount of between approximately 0.5% and approximately 20% of the topical cream by weight. More preferably, the topical pharmaceutical composition of the disclosure contains clonidine at approximately 0.2% of the topical cream by weight, and phenytoin sodium at approximately 5% of the topical cream by weight, preferably phenytoin at approximately 5% of the topical cream by weight.

According to the disclosure, for the relief of pain in a subject the topical pharmaceutical composition of the disclosure comprises at least one selective serotonin reuptake inhibitor, such as paroxetine, in an amount of between approximately 0.5% and approximately 20% of the topical cream by weight together with a therapeutic effect booster phenytoin (e.g., phenytoin sodium) in an amount of between approximately 0.5% and approximately 20% of the topical cream of the disclosure by weight. More preferably, the topical pharmaceutical composition of the disclosure contains paroxetine at approximately 10% of the topical cream by weight, and phenytoin sodium at approximately 10% of the topical cream by weight, preferably phenytoin at approximately 10% of the topical cream by weight.

According to the disclosure, for the relief of pain in a subject the topical pharmaceutical composition of the disclosure comprises at least one serotonin-norepinephrine reuptake inhibitor, such as venlafaxine, in an amount of between approximately 0.5% and approximately 20% of the topical cream by weight together with a therapeutic effect booster phenytoin (e.g., phenytoin sodium) at an amount of between approximately 0.5% and approximately 20% of the topical cream of the disclosure by weight. More preferably, the topical pharmaceutical composition of the disclosure contains venlafaxine at approximately 10% of the topical cream of the disclosure by weight, and phenytoin sodium at approximately 10% of the topical cream of the disclosure by weight, preferably phenytoin at approximately 10% of the topical cream by weight.

According to the disclosure, for the relief of pain in a subject the topical pharmaceutical composition of the disclosure comprises at least one non-steroidal anti-inflammatory drug, such as diclofenac, at an amount of between approximately 0.5% and approximately 20% of the topical cream of the disclosure by weight together with a therapeutic effect booster phenytoin (e.g., phenytoin sodium) at an amount of between approximately 0.5% and approximately 30% of the topical cream of the disclosure by weight, preferably between approximately 0.5% and approximately 20% of the topical cream of the disclosure by weight. More preferably, the topical pharmaceutical composition of the disclosure contains diclofenac at approximately 5% of the topical cream of the disclosure by weight, and phenytoin sodium at approximately 5% of the topical cream of the disclosure by weight, preferably phenytoin at approximately 5% of the topical cream of the disclosure by weight.

According to the disclosure, for the relief of pain in a subject the topical pharmaceutical composition of the disclosure comprises at least one opioid receptor agonist, such as loperamide at an amount of between approximately 0.1% and approximately 20% of the topical cream of the disclosure by weight together with a therapeutic effect booster phenytoin (e.g., phenytoin sodium) at an amount of between approximately 0.5% and approximately 30% of the topical cream of the disclosure by weight, preferably between approximately 0.5% and approximately 20% of the topical cream of the disclosure by weight. More preferably, the topical pharmaceutical composition of the disclosure contains loperamide at approximately 3% of the topical cream of the disclosure by weight, and phenytoin sodium at approximately 5% of the topical cream of the disclosure by weight, preferably phenytoin at approximately 5% of the topical cream of the disclosure by weight.

According to the disclosure, for the relief of pain in a subject the topical pharmaceutical composition of the disclosure comprises at least one local anesthetic lidocaine, at an amount of between approximately 0.5% and approximately 20% of the topical cream of the disclosure by weight together with a therapeutic effect booster phenytoin (e.g., phenytoin sodium) at an amount of between approximately 0.5% and approximately 30% of the topical cream of the disclosure by weight, preferably between approximately 0.5% and approximately 20% of the topical cream of the disclosure by weight. More preferably, the topical pharmaceutical composition of the disclosure contains lidocaine at approximately 5% of the topical cream of the disclosure by weight, and phenytoin sodium at approximately 5% of the topical cream of the disclosure by weight, preferably phenytoin at approximately 5% of the topical cream of the disclosure by weight.

According to the disclosure, for the relief of pain in a subject the topical pharmaceutical composition of the disclosure comprises at least one benzodiazepine, such as diazepam, at an amount of between approximately 0.5% and approximately 20% of the topical cream of the disclosure by weight together with a therapeutic effect booster phenytoin (e.g., phenytoin sodium) at an amount of between approximately 0.5% and approximately 30% of the topical cream of the disclosure by weight, preferably between approximately 0.5% and approximately 20% of the topical cream of the disclosure by weight. More preferably, the topical pharmaceutical composition of the disclosure contains diazepam at approximately 2% of the topical cream of the disclosure by weight, and phenytoin sodium at approximately 5% of the topical cream of the disclosure by weight, preferably phenytoin at approximately 5% of the topical cream of the disclosure by weight.

According to the disclosure, for the relief of pain in a subject the topical pharmaceutical composition of the disclosure comprises at least one barbiturate, such as secobarbital, at an amount of between approximately 0.5% and approximately 20% of the topical cream of the disclosure by weight together with a therapeutic effect booster phenytoin (e.g., phenytoin sodium) at an amount of between approximately 0.5% and approximately 30% of the topical cream of the disclosure by weight, preferably between approximately 0.5% and approximately 20% of the topical cream of the disclosure by weight. More preferably, the topical pharmaceutical composition of the disclosure contains secobarbital at approximately 5% of the topical cream of the disclosure by weight, and phenytoin sodium at approximately 5% of the topical cream of the disclosure by weight, preferably phenytoin at approximately 5% of the topical cream of the disclosure by weight.

According to the disclosure, for the relief of pain in a subject the topical pharmaceutical composition of the disclosure comprises dimethylsulfoxide, at an amount of between approximately 10% and approximately 80% of the topical cream of the disclosure by weight together with a therapeutic effect booster phenytoin (e.g., phenytoin sodium) at an amount of between approximately 0.5% and approximately 30% of the topical cream of the disclosure by weight, preferably between approximately 0.5% and approximately 20% of the topical cream of the disclosure by weight. More preferably, the topical pharmaceutical composition of the disclosure contains dimethylsulfoxide at approximately 50% of the topical cream of the disclosure by weight, and phenytoin sodium at approximately 10% of the topical cream of the disclosure by weight, preferably phenytoin at approximately 5% of the topical cream of the disclosure by weight.

According to the disclosure, for the relief of pain in a subject the topical pharmaceutical composition of the disclosure comprises NMDA-antagonist, such as ketamine, at an amount of between approximately 0.5% and approximately 20% of the topical cream of the disclosure by weight together with a therapeutic effect booster phenytoin (e.g., phenytoin sodium) at an amount of between approximately 0.5% and approximately 30% of the topical cream of the disclosure by weight, preferably between approximately 0.5% and approximately 20% of the topical cream of the disclosure by weight. More preferably, the topical pharmaceutical composition of the disclosure contains ketamine at approximately 10% of the topical cream of the disclosure by weight, and phenytoin sodium at approximately 5% of the topical cream of the disclosure by weight, preferably phenytoin at approximately 5% of the topical cream of the disclosure by weight.

According to the disclosure, for the relief of pain in a subject the topical pharmaceutical composition of the disclosure comprises a cannabinoid, such as cannabidiol, at an amount of between approximately 0.5% and approximately 20% of the topical cream of the disclosure by weight together with a therapeutic effect booster phenytoin (e.g., phenytoin sodium) at an amount of between approximately 0.5% and approximately 20% of the topical cream of the disclosure by weight. More preferably, the topical pharmaceutical composition of the disclosure contains cannabidiol at approximately 4% of the topical cream of the disclosure by weight, and phenytoin sodium at approximately 5% of the topical cream of the disclosure by weight, preferably phenytoin at approximately 5% of the topical cream of the disclosure by weight.

According to the disclosure, for the relief of pain in a subject the topical pharmaceutical composition of the disclosure comprises an anti-epileptic compound, such as pregabalin, at an amount of between approximately 0.5% and approximately 20% of the topical cream of the disclosure by weight together with a therapeutic effect booster phenytoin (e.g., phenytoin sodium) at an amount of between approximately 0.5% and approximately 30%, preferably between approximately 0.5% and approximately 20% of the topical cream of the disclosure by weight of the topical cream of the disclosure by weight. More preferably, the topical pharmaceutical composition of the disclosure contains pregabalin at approximately 10% of the topical cream of the disclosure by weight, and phenytoin sodium at approximately 5% of the topical cream of the disclosure by weight, preferably phenytoin at approximately 5% of the topical cream of the disclosure by weight.

Description of cases: Phenytoin as an effect booster for the analgesic effect of topical cream containing an analgesic (ketamine, baclofen, amitriptyline, loperamide)

One embodiment of the disclosure is the pharmaceutical composition according to the disclosure, wherein the one or more further (co-)analgesics is/are muscle relaxant baclofen, dantrolene, tizanidine, carisoprodol, or cyclobenzaprine, tricyclic antidepressant amineptine, amitriptyline, amitriptylinoxide, butriptyline, demexiptiline, dibenzepin, dimetacrine, dothiepin, fiuacizine, iprindole, clomipramine, desipramine, desmethylamitriptyline, doxepin, imipramine, imipraminoxide, trimipramine, lofepramine, maprotiline, melitracen, metapramine, norclolipramine, nortriptyline, noxiptilin, opipramol, perlapine, pizotyline, propizepine, protriptyline, quinupramine, reboxetine, or tianeptine, or a derivative, prodrug, stereoisomer, and/or salt thereof, tetracyclic antidepressant amoxapine, aptazapine, ciclazindol, esmirtazapine, loxapine, mazindol, metralindole, maprotiline, mianserin, mirtazapine, oxaprotiline, pirlindole, setiptiline or a derivative, prodrug, stereoisomer, and/or salt thereof, alpha 2-adrenergic agonist amidephrine, amitraz, anisodamine, apraclonidine, brimonidine, cirazoline, clonidine, detomidine, dexmedetomidine, epinephrine, ergotamine, etilefrine, fadolmidine, guanabenz, guanethidine, guanfacine, guanoxabenz, indanidine, lofexidine, medetomidine, mephentermine, metaraminol, methoxamine, methyldopa, mivazerol, naphazoline, norepinephrine, norfenefrine, octopamine, oxymetazoline, phenylpropanolamine, rilmenidine, romifidine, synephrine, talipexole, xylazine, or a derivative, prodrug, stereoisomer, and/or salt thereof, selective serotonin reuptake inhibitor paroxetine, cericlamine, citalopram, dapoxetine, escitalopram, fluoxetine, fluvoxamine, indalpine, paroxetine, sertraline, zimelidine, diastereoisomers thereof, a derivative, prodrug, stereoisomer, or salt thereof, serotonin-noradrenalin reuptake inhibitor duloxetine, desvenlafaxine, levomilnacipran, milnacipran, sibutramine, venlafaxine, or a derivative, prodrug, stereoisomer, and/or salt thereof, non-steroidal anti-inflammatory drug diclofenac, duloxetine, desvenlafaxine, levomilnacipran, milnacipran, sibutramine, venlafaxine, or a derivative, prodrug, stereoisomer, and/or salt thereof, opioid receptor agonist loperamide, opioid alfentanil, allylprodine, alphaprodine, anileridine, benzyl-morphine, bezitramide, buprenorphine, butorphanol, clonitazene, codeine, cyclazocine, desomorphine, dextromethorphan, dextromoramide, dezocine, diampromide, diamorphone, dihydrocodeine, dihydromorphine, dimenoxadol, dimepheptanol, dimethylthiambutene, dioaphetylbutyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, loperamide, meperidine (pethidine), meptazinol, metazocine, methadone, metopon, morphine, myrophine, nalbuphine, narceine, nicomorphine, norlevorphanol, normethadone, nalorphine, normorphine, norpinanone, opium, oxycodone, oxymorphone, papaveretum, pentazocine, phenadoxone, phenomorphan, phanazocine, phenoperidine, piminodine, piritramide, propheptazine, promedol, properidine, propiram, propoxyphene, sulfentanil, tilidine, tramadol, tapentadol, axomadol, faxeladol, diastereoisomers thereof, or a derivative, prodrug, stereoisomer, and/or salt thereof, local anesthetic amethocaine, articaine, benzocaine, bupivacaine, chloroprocaine, cinchocaine, cocaine, cyclomethycaine, dibucaine, dimethocaine, etidocaine, ethyl aminobenzoate, eugenol, levobupivacaine, lidocaine, menthol, mepivacaine, neosaxitoxin, oxethazaine, oxybuprocaine, piperocaine, prilocaine, propoxycaine, procaine, proparacaine, ropivacaine, saxitoxin, tetracaine, tetrodotoxin, trimecaine, diastereoisomers thereof, or a derivative, prodrug, stereoisomer, and/or salt thereof, benzodiazepine adinazolam, alprazolam, bentazepam, bretazenil, bromazepam, brotizolam, camazepam, cinazepam, cinolazepam, chlordiazepoxide, climazolam, clobazam, clonazepam, clonazolam, clorazepate, clorazepate, clotiazepam, cloxazolam, delorazepam, diazepam, diclazepam, ethyl carfluzepate, estazolam, etizolam, ethyl loflazepate, flubromazepam, flubromazolam, flunitrazepam, flurazepam, flutazolam, halazepam, ketazolam, loprazolam, lorazepam, lormetazepam, medazepam, mexazolam, midazolam, nifoxipam, nimetazepam, N-desmethyladinazolam, nitrazepam, nordiazepam, oxazepam, phenazepam, pinazepam, prazepam, premazepam, pyrazolam, quazepam, rilmazafone, temazepam, tetrazepam, thienalprazolam, triazolam, derivative, flumazenil, eszopiclone, zaleplon, zolpidem, zopiclone or a prodrug, stereoisomer, and/or salt thereof, barbiturate allobarbital, amobarbital, aprobarbital, alphenal, barbital, barbexaclone, brallobarbital, butabarbital, butalbital, butallylonal, butobarbital, crotylbarbital, cyclobarbital, cyclopal, desoxyphenobarbital, diphenylbarbituric acid, ethallobarbital, febarbamate, heptabarbital, hexethal, hexobarbital, mephobarbital, metharbital, methohexital, methylphenobarbital, narcobarbital, nealbarbital, pentobarbital, phenobarbital, probarbital, propallylonal, proxibarbal, proxibarbital, reposal, secbutabarbital, secobarbital, sigmodal, talbutal, thialbarbital, thiamylal, thiobarbital, thiobutabarbital, thiopental, valofane, vinbarbital, vinylbital, or a derivative, prodrug, stereoisomer, and/or salt thereof, dimethylsulfoxide, NMDA-receptor antagonist (l, r or racemic) ketamine, amantadine, aptiganel, caroverine, dextrorphan, dextromethorphan, fullerenes, ibogaine, ketamine, lidocaine, memantine, dizocilpine, neramexane, norketamin, delucemine, 3-fluoro-γ-(3-fluorophenyl)-N-methyl-benzenepropanamine hydrochloride, phencyclidine, tiletamine, remacemide decahydro-6-(phosphonomethyl)-3-isoquinolinecarboxylic acid, (3 S,4aR,6S,8aR)-decahydro-6-(phosphonomethyl)-3-isoquinolinecarboxylic acid, (2R,4S)-rel-4-(1H-tetrazol-5-ylmethyl)-2-piperidine carboxylic acid, α-amino-2-(2-phosphonoethyl)-cyclohexanepropanoic acid, glutathione, carbamathione, 5-phosphono-norvaline, 4-(3-phosphonopropyl)-2-piperazine-carboxylic acid, seifotel, cis-4(phonomethyl)-2-piperidine-carboxylic acid, (3E)-2-amino-4-methyl-5-phosphono-3-pentenoic acid, (3E)-2-amino-4-methyl-5-phosphono-3-pentenoic acid, 1-ethyl ester, (αS)-α-amino-2'-chloro-5-(phosphonomethyl)-[1,1'-biphenyl]-3-propanoic acid, S-nitrosoglutathione, camprosate, arcaine, conantokin-G, eliprodil, haloperidol, ifenprodil, traxoprodil, (R,S)-α-(4-hydroxyphenyl)-β-methyl-4-(phenylmethyl)-1-piperidine propanol, aminocyclopropanecarboxylic acid, 7-chlorokynurenic acid, D-cycloserine, gavestinel, 4,6-dichloro-3-[(E)-(2-oxo-1-phenyl-3-pyrrolidinylidene) methyl]-1H-indole-2-carboxylic acid monosodium salt, licostinel, 8-chloro-2,3-dihydropyridazino[4,5-b]quinoline-1,4-dione 5-oxide 2-hydroxy-N,N,N-trimethylethanaminium salt, 7-chloro-4-hydroxy-3-(3-phenoxyphenyl)-2(1H)-quinolinone, 3-amino-1-hydroxy-2-pyrrolidinone, 7-chloro-4-hydroxy-2-(4-methoxy-2-methylphenyl)-1,2,5,10-tetra-hydropyridanizo[4,5-b]quinoline-1,10-dione, sodium salt, or a derivative, prodrug, stereoisomer, and/or salt thereof, N-acylethanolamide N-arachidonoylethanolamide, docosahexaenoylethanolamide, oleoylethanolamide, palmitoylethanolamide, stearoylethanolamide, or a derivative, prodrug, stereoisomer, and/or salt thereof cannabinoid cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, dronabinol, amandamide, nabilone, or a derivative, prodrug, stereoisomer, and/or salt thereof, and/or anti-epileptic compound acetazolamide, beclamide, brivaracetam, carbamazepine, divalproex sodium, eslicarbazepine acetate, ethadionelamotrigine, ethosuximide, felbamate, gabapentin, lamotrigine, levetiracetam, mesuximide, methazolamide, oxcarbazepine, paramethadione, phenacemide, pheneturide, phensuximide, potassium bromide, pregabalin, perampanel, primidone, progabide, seletracetam, sodium valproate, sultiame, tiagabine, topiramate, trimethadione, valnoctamide, valpromide, valproic acid, vigabatrin, zonisamide, or a derivative, prodrug, stereoisomer, or salt thereof, or a combination thereof.

One embodiment of the disclosure is the method according to the disclosure, wherein the first co-analgesic and/or the at least one further (co-)analgesic of step b) are filtered through a fine-mesh screen of between 30 and 50 mesh, preferably about 40 mesh, before mixing the (co-)analgesics in step e) with the pharmaceutically acceptable carrier.

All compounds applied in the pharmaceutical composition of the disclosure are accurately weighed using an approved weighing scale. The required amount of water is measured using an approved cylindrical graduate. Optionally, the active pharmaceutical ingredients, i.e., the first co-analgesic and/or the at least one further (co-)analgesic of step b) of the method of the disclosure (e.g., phenytoin sodium, phenytoin) is/are first filtered through a fine-mesh screen of between 30 and 50 mesh, and preferably through a mesh-screen of 40 mesh, into a mortar. The benefit of first filtering the active pharmaceutical ingredient(s), of which, for example, phenytoin sodium or phenytoin, has/have the tendency to agglomerate, is that, for example, the phenytoin or the phenytoin sodium is finely and homogenously distributed facilitating subsequent optimal dissolving in the selected formulation base.

According to the method for preparing a pharmaceutical composition of the disclosure, the oil-soluble compounds are heated to a temperature of between 20° C. to 95° C., or, for example, to about 95° C., and mixed, for example, mixed together in a stainless steel bowl of a stirring device (phase A): e.g., paraffinum liquidum, white Vaseline®. Then, for example, ceteareth and cetostearyl alcohol, which are also first heated to a temperature of between 20° C. to 95° C., are added to the e.g., paraffinum liquidum, white Vaseline®. See in the EXAMPLES section for examples of applicable oil-soluble compounds of the disclosure. The water-soluble compounds of a cream base according to the disclosure (e.g., acidum ascorbicum, citric acid monohydrate, sodium hydroxide and sodium dihydrogen phosphate dehydrate) are added while mixing to water with a temperature of between 20° C. to 95° C. (phase B). Optionally, at this stage, the pH is adjusted to between 4.0 and 6.5, preferably at about 4.5 to 6.2, according to the method of the disclosure. Before combining Phase A and Phase B, and mixing Phase A and Phase B, the two phases are brought at about the same temperature, preferably the same temperature. The temperature of Phase A and Phase B before combining and mixing the phases is between room temperature and about 95° C., preferably between about 20° C. and about 95° C., more preferably the temperature is about 70° C. Phase B is slowly poured in phase A and cooled down while stirring until the temperature is, for example, decreased to about 56° C., preferably 56° C., according to the method of the disclosure. Alternatively, Phase B is slowly poured in phase A and cooled down while stirring until the temperature is, for example, decreased to about 20° C., preferably room temperature, according to the method of the disclosure. Herewith, the pharmaceutically acceptable carrier for topical use is provided, for application in the pharmaceutical composition of the disclosure.

Then, the first co-analgesic and the at least one further (co-)analgesic are added to the mixture, i.e., the pharmaceutically acceptable carrier for topical use, while stirring for between 5 to 20 minutes, preferably for about 10 minutes according to the method of the disclosure, for example, by using a high-shear homogenizer. The temperature is preferably about 20° C. or about room temperature during the adding of the active pharmaceutical ingredient to the pharmaceutically acceptable carrier. Optionally, at this stage, the pH is adjusted to between 4.0 and 6.5, preferably at about 4.5 to 6.2, according to the method of the disclosure, or the pH is adjusted to between 10.0 and 12.0, preferably at about 11.0 to 11.5, according to the method of the disclosure. The compositions of the disclosure are then, for example, packaged in 30 grams aluminum tubes and stored according to methods well-known in the art.

A pharmaceutical composition for use in the treatment of peripheral neuropathic pain according to the disclosure having a pH of between 4.0 and 6.5 is preferred. It is common general knowledge that in general compositions applied to the skin of patients having such a pH are mild to the skin of patients, with regard to the pH of between 4.0 and 6.5.

See the Examples sections for a comparative study with a cream according to the disclosure, comprising phenytoin as the first co-analgesic and at least one further (co-)analgesic and having a pH of about 5, and a second cream according to the disclosure, comprising phenytoin sodium as the first co-analgesic and at least one further (co-)analgesic and having a pH of about 11. These two creams of the disclosure were equally effective with regard to the beneficial, pain-reducing effect when applied to patients suffering from peripheral neuropathic pain. Patients treated with any of these two creams did not report any side effects related to the side of cream application on the skin.

Besides for treatment of neuropathic pain, the pharmaceutical composition of the present disclosure is used to treat inflammatory pain, musculoskeletal pain, pain due to spasms, muscular headaches and tension type headaches, migraines, cluster headaches, atypical facial pains, referred pain, vulvodynia, proctodynia, and other chronic pain states, according to the disclosure.

One embodiment of the disclosure is the pharmaceutical composition for use in the treatment of chronic pain according to the disclosure, wherein the pharmaceutical composition induces reduction of pain without inducing side effects. It is part of the disclosure that the pharmaceutical composition of the disclosure reduces neuropathic pain, treat inflammatory pain, musculoskeletal pain, pain due to spasms, muscular headaches and tension type headaches, migraines, cluster headaches, atypical facial pains, referred pain, vulvodynia, proctodynia, and other chronic pain states, without inducing side effects, according to the disclosure.

The faster onset of action, i.e., pain reduction in a patient, by adding phenytoin to an analgesic according to the disclosure, is due to a synergistic effect of phenytoin and the at least one further active compound, i.e., (co-)analgesic compound in the pharmaceutical composition of the disclosure.

In the EXAMPLES, below, for Cases 2 and 9, amitriptyline and ketamine applied separately led to an onset of action in about 10 to 15 minutes, while combining either amitriptyline, or ketamine with phenytoin led to a surprisingly fast onset of action of as soon as after less than 5 minutes.

The present disclosure will be illustrated further by means of the following non-limiting Examples.

EXAMPLES

Case 1. Trigeminal Neuralgia (Ketamine 10% Cream & Phenytoin 10%)

A 52-year-old man has suffered since 2012 from trigeminal neuralgia, the third left branch having been lesioned during or after a lower jaw correction operation. He complained of tingling, pins and needles and numbness in the affected area. Allodynia was also present: worsening of his complaints by wind or light stroke, pain ranged 5 to 6 on the 11-point numerical rating scale (NRS). His current medication was venlafaxine 75 mg once daily, though that induced nausea. During the first visit ketamine 10% cream reduced his complaints completely, though 4 days later the complaints returned to the same intensity of pain. Ketamine 10% cream resulted in only a slight reduction of the allodynia: from 6 to 5 on the NRS. During the second visit the addition of the booster phenytoin 10% cream to ketamine 10% cream, resulted surprisingly in complete reduction of the complaints and the allodynia.

The pharmaceutical composition of the disclosure containing 10% phenytoin sodium and 10% ketamine HCl by weight of the cream in a topical cream, further consisted of the skin penetration enhancer decylis oleas (16% by weight of the cream). The patient applied about 0.4 FTU at the left lower jaw during each administration, i.e., in total about 0.2 gram to 0.25 gram of the cream, thus containing between about 0.02 gram to 0.025 gram of the phenytoin sodium and about 0.02 gram to 0.025 gram of the ketamine HCl. The patient applied the cream of the disclosure 3 times per day. The patient applied the cream of the disclosure during a period of 2 months. It is intended that the patient continues using the cream of the disclosure, chronically, during his lifespan, i.e., for the rest of his life. The phenytoin sodium and the ketamine HCl were sieved using a 40 mesh sieve, in the method for preparing a pharmaceutical composition for use in the treatment of chronic pain according to the disclosure.

Case 2. Small Fiber Neuropathy (Ketamine 10% Cream & Phenytoin 10%)

A 57-year-old man has suffered since 2014 from symptoms based on small fiber neuropathy as diagnosed by the neurologist. He was treated with pregabalin, without sufficient pain reduction, due to the low dose pregabalin treatment regime, as the patient had a compromised renal function. The patient complained of burning pain in feet and hands, and tingling and coldness. Pain was further provoked by standing and walking.

Single blind (only the physician knew which cream was applied) one part of the neuropathic pain area on the most painful foot was treated with ketamine 10% cream, resulting in a slight reduction of burning pain, after 10 minutes, though the tingling aggravated. Another part of the most painful foot was treated with phenytoin 10% cream, resulting in a reduction of burning pain after around 10 minutes, as well as of reduction in coldness. Adding the phenytoin cream immediately after the application of the ketamine cream resulted in a clear improved pain reduction within 5 minutes, and pain was reduced in total more than 50%, from NRS 6.5 to 3. Surprisingly, the aggravated tingling provoked by ketamine disappeared totally after the application of the phenytoin cream, and the overall finding was expressed by the patient as: "it all feels now peaceful and quit in the area where the two creams were applied." Walking and standing provoked much less pain and the patient reported a 40% improvement in pain while standing and walking. The improvement lasted for 24 hours.

Thus, without the patient knowing which cream was applied, ketamine 10% cream reduced pain but did not reduce tingling and coldness, and even seemed to enhance some tingling, while phenytoin 10% cream could decrease the tingling, as well as the coldness, and, most importantly and surprisingly, the phenytoin cream enhanced the pain killing effect of ketamine, had a very fast action of onset, around 5 minutes, and the combined analgesic effect after application of co-analgesic phenytoin and analgesic ketamine lasted much longer than with ketamine 10% cream alone (which effect lasts during only some hours), namely 24 hours.

The pharmaceutical composition of the disclosure containing 10% phenytoin sodium and 10% ketamine HCl by weight of the cream in a topical cream, further consisted of the skin penetration enhancer decylis oleas (16% by weight of the cream). The patient applied 0.8 FTU at each foot during each administration, i.e., in total about 0.8 gram to 1.0 gram of the cream, thus containing between about 0.08 gram to 0.1 gram of the phenytoin sodium and about 0.08 gram to 0.1 gram of the ketamine HCl. The patient applied the cream of the disclosure 1 time per day. The patient applied the cream of the disclosure during a period of 4 months. It is intended that the patient continues using the cream of the disclosure, chronically, during his lifespan, i.e., for the rest of his life. The phenytoin sodium and the ketamine HCl were sieved using a 40 mesh sieve, in the method for preparing a pharmaceutical composition for use in the treatment of chronic pain according to the disclosure.

Case 3. Diabetic Neuropathic Pain (Ketamine 10% Cream & Phenytoin 10%)

A 69-year-old man has suffered since 2007 from peripheral neuropathic pain in both feet due to Diabetes Mellitus type II. He scored his average pain as 9 on the NRS. His pain was characterized by burning, electric shocks, tingling, pins and needles, and allodynia upon soft stroking. Especially his allodynia on his left foot was bothering him in the night. Pregabalin 75 mg twice daily did not have any effect. The patient was now administered ketamine 10% cream (Keppel Hesselink J M, Kopsky D J (2013)). This resulted in a reduction of pain from 9 to a 5.5 on the NRS, with an onset of effect after 25 minutes and duration of pain reduction of 6.5 hours. Adding phenytoin 10% cream to ketamine 10% cream resulted in an onset of effect after only 5 minutes, a large reduction of pain to 2.5 on the NRS, and a long-lasting duration of effect of 11 hours. This case surprisingly demonstrates that phenytoin 10% and ketamine 10% by weight of the cream of the disclosure has a synergistic effect on the onset of pain-reduction, enhances the reduction of pain intensity and prolongs the pain reducing effect, compared to 10% phenytoin by weight of the cream alone, or 10% ketamine by weight of the cream alone.

The pharmaceutical composition of the disclosure containing 10% phenytoin sodium and 10% ketamine HCl by weight of the cream in a topical cream, further consisted of the skin penetration enhancer decylis oleas (16% by weight of the cream). The patient applied 0.5 FTU at each foot during each administration, i.e., in total about 0.5 gram to 0.6 gram of the cream, thus containing between about 0.05 gram to 0.06 gram of the phenytoin and about 0.05 gram to 0.06 gram of the ketamine HCl. The patient applied the cream of the disclosure 2 times per day. The patient applied the cream of the disclosure during a period of 5 months. It is intended that the patient continues using the cream of the disclosure, chronically, during his lifespan, i.e., for the rest of his life. The phenytoin sodium and the ketamine HCl were sieved using a 40 mesh sieve, in the method for preparing a pharmaceutical composition for use in the treatment of chronic pain according to the disclosure.

Case 4. Chronic Idiopathic Axonal Polyneuropathy (Clonidine 0.2% Cream & Phenytoin 5%)

A 63-year-old man has suffered since 2012 of chronic idiopathic axonal polyneuropathy with pain in both his feet with the following characteristics: burning, tingling, pins and needles and numbness. He scored his average pain as 8 on the NRS. Oral amitriptyline did not have any pain relieving effect. Topical clonidine 0.2% cream reduced tingling, pins and needles after 15 minutes from 8 to 5 on the NRS, and burning from 8 to 2.5 on the NRS. The duration of the effect was 6 hours; this was not enough not to wake up from the pain at night. He applied the topical analgesic 3 times daily. After adding co-analgesic phenytoin 5% cream to the analgesic clonidine 0.2% cream according to the disclosure, the onset of effect was already after 5 minutes, the reduction of tingling, pins and needles was as large as from 8 to 2.5 on the NRS, and burning reduced even from 8 to 0 on the NRS. The duration of the effect was prolonged to up to 10 hours, which improvements permitted him to sleep the whole night through without waking up due to pain. He reduced the administration of the topical cream of the disclosure from 3 to 2 times daily.

The pharmaceutical composition of the disclosure containing 5% phenytoin sodium and 0.2% clonidine HCl by weight of the cream in a topical cream, further consisted of the skin penetration enhancer cetostearyl alcohol (6.8% by weight of the cream). The patient applied 0.8 FTU at each foot during each administration, i.e., in total about 0.8 gram to 1.0 gram of the cream, thus containing between about 0.04 gram to 0.05 gram of the phenytoin sodium and about 0.8 milligram to 1 milligram of the clonidine HCl. The patient applied the cream of the disclosure 2 times per day. The patient applied the cream of the disclosure during a period of 3 months. It is intended that the patient continues using the cream of the disclosure, chronically, during his lifespan, i.e., for the rest of his life. The phenytoin sodium and the clonidine HCl were sieved using a 40 mesh sieve, in the method for preparing a pharmaceutical composition for use in the treatment of chronic pain according to the disclosure.

Case 5. Trigeminal Neuralgia (Baclofen 5% Cream & Phenytoin 10%)

A 69-year-old man has suffered since 2011 from trigeminal neuralgia, the second right branch, after an accident. He complained of tingling that worsens when talking or with cold wind. The medication was pregabalin 150 mg twice daily and buprenorfine plasters 10 mcg/hour. Baclofen 5% cream reduced pain within 10 minutes from 7 to 2 on the NRS. The effect, however, was only short and transient: 1.5 hours. He could reduce the buprenorphine plasters to 5 mcg/hour. The addition of 10% phenytoin sodium by weight of the cream, providing the pharmaceutical composition of the disclosure by the method of the disclosure, surprisingly prolonged the effect with 3 hours. Also the combination of phenytoin 10% and baclofen 5% had a synergistic analgesic effect with a complete reduction of pain to 0 on the NRS.

The pharmaceutical composition of the disclosure containing 10% phenytoin sodium and 5% baclofen by weight of the cream in a topical cream, further consisted of the skin penetration enhancer decylis oleas (17% by weight of the cream). The patient applied 0.2 FTU at the right cheek during each administration, i.e., in total about 0.1 gram of the cream, thus containing between about 10 milligram of the phenytoin sodium and about 5 milligram of the baclofen. The patient applied the cream of the disclosure 6 times per day. The patient applied the cream of the disclosure during a period of 3 months. It is intended that the patient continues using the cream of the disclosure, chronically, during his lifespan, i.e., for the rest of his life. The phenytoin sodium and the baclofen were sieved using a 40 mesh sieve, in the method for preparing a pharmaceutical composition for use in the treatment of chronic pain according to the disclosure.

Case 6. Chemotherapy-Induced Polyneuropathy (CIPN) (Baclofen 5% Cream & Phenytoin 10%)

A 67-year-old man, has suffered since 2015 of CIPN, resulting from the treatment of oxaliplatin because of a metastasized rectal carcinoma. He experienced tingling, pins and needles and numbness in both feet. He also complained of coldness of the feet. He scored his complaints with a 5 on the NRS. The combination cream of lidocaine 3% together with isosorbide dinitrate 0.4% cream reduced his pain to a 4 on the NRS. To first analyze whether a cream comprising 10% phenytoin sodium by weight of cream did have some pain reducing effects, compared to the pharmaceutical composition of the disclosure consisting of 10% phenytoin and 5% baclofen by weight of cream as the active pharmaceutical ingredients, cream with 10% phenytoin by weight of cream was applied on the left foot, and the pharmaceutical composition of the disclosure was applied on the right foot. He experienced a pain reduction of the left foot from a 4 to a 3 on the NRS and a surprisingly large pain reduction of the left foot from a 4 to a 1 on the NRS. The booster phenytoin 10% cream applied alone on the left foot had only a slight symptom reducing effect, while upon administering the pharmaceutical composition of the disclosure, a clear symptom reduction was experienced.

The pharmaceutical composition of the disclosure containing 10% phenytoin sodium and 5% baclofen by weight of the cream in a topical cream, further consisted of the skin penetration enhancer decylis oleas (17% by weight of the cream). The patient applied 0.8 FTU at each foot during each administration, i.e., in total about 0.8 gram to 1 gram of the cream, thus containing between about 0.08 gram to 0.1 gram of the phenytoin sodium and about 0.04 gram to 0.05 gram of the baclofen. The patient applied the cream of the disclosure 3 times per day. The patient applied the cream of the disclosure during a period of 2 months. It is intended that the patient continues using the cream of the disclosure, chronically, during his lifespan, i.e., for the rest of his life. The phenytoin sodium and the baclofen were sieved using a 40 mesh sieve, in the method for preparing a pharmaceutical composition for use in the treatment of chronic pain according to the disclosure.

Case 7. Neuropathic Pain after Guillain-Barre Syndrome (Baclofen 5% Cream & Phenytoin 5%)

A 63-year-old man experienced Guillain-Barre syndrome in 1980. He recovered with minor sequelae: numbness of the feet, reduced facial expressions, and diminished motor function of the left hand. In 2011, he experienced stabbing pain in his big left toe (average pain score of 8.5 on the NRS), especially at night time after taking off his shoes, which prevented him from sleeping. Oral pregabalin had a pain reducing effect, though he experienced bothersome side effects: anxiety and depression. Baclofen 5% cream clearly had some effect on his pain. The first 10 minutes after application the pain aggravated where after the pain vanished completely. He had to apply baclofen 5% cream 2 to 4 times in the night. Administering the pharmaceutical composition of the disclosure comprising as the active pharmaceutical ingredients the co-analgesic phenytoin at 5% by weight of the cream and the analgesic baclofen at 5% by weight of the cream resulted in the absence of aggravation of pain, and direct pain reduction upon administration of the cream of the disclosure. Most of the nights the patient could reduce the times of application of the topical pharmaceutical composition of the disclosure to only one. His quality of sleep was improved considerably.

The pharmaceutical composition of the disclosure containing 5% phenytoin and 5% baclofen by weight of the cream in a topical cream, further consisted of the skin penetration enhancer cetostearyl alcohol (6.3% by weight of the cream). The patient applied 0.2 FTU at his left big toe during each administration, i.e., in total about 0.1 gram of the cream, thus containing between about 5 mg milligram of the phenytoin and about 5 milligram of the baclofen. The patient applied the cream of the disclosure mostly one time per night. The patient applied the cream of the disclosure during a period of 5 months. It is intended that the patient continues using the cream of the disclosure, chronically, during his lifespan, i.e., for the rest of his life. The phenytoin and/or the baclofen were sieved using a 40 mesh sieve, in the method for preparing a pharmaceutical composition for use in the treatment of chronic pain according to the disclosure.

Case 8. Neuropathic Pain Due to Partial Spinal Cord Injury (Baclofen 5%/Amitriptyline 10% & Phenytoin 5% Cream)

A 61-year-old man suffers from a partial spinal cord injury on the level of C5/C6 due to a motor cycle accident in 2002. Since his accident, he suffers from chronic pain in several areas: burning and dull pain on the left side of the back, stabbing pain in the C7 distribution area of the left arm, and tingling in his feet. He scores his average pain with a 9 on the NRS. From oral medication, such as pregabalin and gabapentin, he experienced too much side effects. The burning and dull pain in the back and tingling in his feet could be diminished with baclofen 5% cream from 9 to 6 on the NRS. The stabbing pain in the C7 distribution area of the arm reacted on amitriptyline 10% cream with an equivalent reduction from 9 to 6 on the NRS. The onset of effect of both topical analgesics was after 15 minutes and the effect lasted for 2.5 hours. Adding phenytoin 5% to both topical analgesic creams resulted in a more pronounced reduction of pain. Phenytoin 5% and baclofen 5% cream reduced burning and dull pain from 9 to 4 on the NRS, and tingling from 9 to 2 on the NRS. Phenytoin 5% and amitriptyline 10% cream reduced the stabbing pain from 9 to 3 on the NRS. Also the onset of effect was faster: 5 minutes. Finally, the duration of effect was doubled: 5 hours.

The pharmaceutical composition of the disclosure containing 5% phenytoin sodium and 5% baclofen by weight of the cream in a topical cream, further consisted of the skin penetration enhancer decylis oleas (18% by weight of the cream). The patient applied 0.8 FTU at each foot and about 0.5 FTU on his left side of his back during each administration, i.e., in total about 1.1 gram to 1.3 gram of the cream, thus containing between about 55 milligram to 65 milligram of the phenytoin sodium and about 55 milligram to 65 milligram of the baclofen.

The pharmaceutical composition of the disclosure containing 5% phenytoin sodium and 10% amitriptyline by weight of the cream in a topical cream, further consisted of the skin penetration enhancer decylis oleas (17% by weight of the cream). The patient applied 0.5 FTU at C7 distribution area of his left arm during each administration, i.e., in total about 0.3 gram of the cream, thus containing between about 15 milligram of the phenytoin sodium and about 30 milligram of the amitriptyline.

The patient applied both analgesic creams of the disclosure 4 times per day. The patient applied both analgesic creams of the disclosure during a period of 5 months. It is intended that the patient continues using the cream of the disclosure, chronically, during his lifespan, i.e., for the rest of his life. The phenytoin and/or the baclofen were sieved using a 40 mesh sieve, in the method for preparing a pharmaceutical composition for use in the treatment of chronic pain according to the disclosure.

Case 9. Chemotherapy-Induced Polyneuropathy (Amitriptyline 10% & Phenytoin 5% Cream)

A 48-year-old man with acute leukemia was treated with Mitroxantrone and Etoposide in July 2014. The chemotherapy caused hand-foot syndrome (redness and edema), with neuropathic pain in the feet. He described his pain as burning, tingling, pins and needles, and scored his pain with an 8.5 on the NRS in November 2015. Physical examination revealed hypesthesia for pinprick and touch and allodynia. The pain was diagnosed as neuropathic pain due to chemotherapy. Amitriptyline 10% cream reduced the pain considerably, from 8.5 to 0, with an onset of effect of 8 minutes after application. A drawback of the amitriptyline 10% cream was that the neuropathic pain recurred after 1 to 1.5 hours. In October 2016, he scored his neuropathic pain with a 6 on the NRS and received phenytoin 5% cream, which also resulted in complete disappearance of the neuropathic pain, though for a longer period of time: 3.5 hours, with an onset of effect of 15 minutes after application. The combination of phenytoin 5% and amitriptyline 10% resulted in complete disappearance of the pain, with a surprisingly long prolonged effect of in total 8 hours and a surprisingly short time period for the onset of effect of as soon as already after 3 minutes. The addition of phenytoin 10% to amitriptyline 10% prolonged the duration of pain relief even longer: a surprisingly long time period of 10 hours. He could sleep again the whole night without being disturbed.

The pharmaceutical composition of the disclosure containing 5% phenytoin and 10% amitriptyline HCl by weight of the cream in a topical cream, further consisted of the skin penetration enhancer decylis oleas (17% by weight of the cream). The patient applied 0.8 FTU at each foot during each administration, i.e., in total about 0.8 gram to 1 gram of the cream, thus containing between about 0.04 gram to 0.05 gram of the phenytoin and about 0.08 gram to 0.1 gram of the amitriptyline HCl. The patient applied the cream of the disclosure 2 times per day. The patient applied the cream of the disclosure during a period of 2 months.

The pharmaceutical composition of the disclosure containing 10% phenytoin and 10% amitriptyline HCl by weight of the cream in a topical cream, further consisted of the skin penetration enhancer decylis oleas (16% by weight of the cream). The patient applied 0.8 FTU at each foot during each administration, i.e., in total about 0.8 gram to 1.0 gram of the cream, thus containing between about 0.08 gram to 0.1 gram of the phenytoin and about 0.08 gram to 0.1 gram of the amitriptyline HCl. The patient applied the cream of the disclosure 1 to 2 times per day. The patient applied the cream of the disclosure during a period of 1 month.

It is intended that the patient continues using the cream of the disclosure, chronically, during his lifespan, i.e., for the rest of his life. The phenytoin and the amitriptyline HCl were sieved using a 40 mesh sieve, in the method for preparing a pharmaceutical composition for use in the treatment of chronic pain according to the disclosure.

Case 10. Chronic Idiopathic Axonal Polyneuropathy (Loperamide 5% & Phenytoin 10%)

A 63-year-old man has suffered since 2013 of neuropathic pain due to chronic idiopathic axonal polyneuropathy. He complained of pain in both feet characterized as burning, tingling, pins and needles, and numbness. He scored his pain with a 7 on the NRS, despite his pain medication: amitriptyline 25 mg once daily, and oxycodone 10 mg twice daily. Pregabalin did not have any effect. Physical examination revealed loss of vibration sense up to the knees, absence of ankle jerk reflexes, loss of temperature sensation up to 20 cm beneath the knees, hypesthesia for pinprick and touch and allodynia. Baclofen 5% cream and amitriptyline 10% cream could reduce his pain from 7 to 5 on the NRS. Loperamide 5% could reduce his pain completely, though the pain reducing effect lasted only about 2.5 hours. The onset of effect was within 30 minutes. Adding phenytoin 10% to loperamide 5% cream could prolong the pain relieving effect to 4.5 hours. He could reduce his oxycodone to 10 mg once daily.

The pharmaceutical composition of the disclosure containing 10% phenytoin and 5% loperamide HCl by weight of the cream in a topical cream, further consisted of the skin penetration enhancer decylis oleas (17% by weight of the cream). The patient applied 0.8 FTU at each foot during each administration, i.e., in total about 0.8 gram to 1.0 gram of the cream, thus containing between about 0.08 gram to 0.1 gram of the phenytoin and about 0.04 gram to 0.05 gram of the loperamide HCl. The patient applied the cream of the disclosure 1 to 2 times per day. The patient applied the cream of the disclosure during a period of 1 month. It is intended that the patient continues using the cream of the disclosure, chronically, during his lifespan, i.e., for the rest of his life. The phenytoin and the loperamide HCl were sieved using a 40 mesh sieve, in the method for preparing a pharmaceutical composition for use in the treatment of chronic pain according to the disclosure.

None of the above-described patients of cases 1 to 10 reported any local or systemic side effects upon administering the pharmaceutical compositions of the disclosure.

Case 11. Comparison of the Combinations Ketamine 10% with Phenytoin 5%, and Amitriptyline 10% with Phenytoin 5%

A 65-year-old man has suffered since 1997 from tingling, pins and needles, and burning due to Chronic Idiopathic Axonal Polyneuropathy (CIAP) (diagnosed in 2014). He scored the pain a 7 to 8 on the NRS. Physical examination revealed absence of knee and anklejerk reflexes and warmth cold discrimination disrupted until his knees. At the time of testing of analgesic creams, he scored his pain a 6 on the NRS. On the left foot and single-blind the combination of phenytoin 5% with ketamine 10% cream was applied, on the right foot the combination of phenytoin 5% with amitriptyline 10% was applied. After 4 minutes the onset of effect was noticed by the patient for both creams. The combination phenytoin 5% with ketamine 10% worsened the pain and he scored the pain a 7 on the NRS. However, the combination of phenytoin 5% with amitriptyline 10% reduced the pain to a score of 4 on the NRS. Thus, this single-blind test showed superiority of the combination combined of phenytoin 5% with amitriptyline 10% over phenytoin 5% with ketamine 10% cream. Thus, the superior combination phenytoin 5% with amitriptyline 10% was subsequently prescribed to the patient.

Case 12. Comparison of Several Combinations Showing Superiority of Phenytoin 5% with Amitriptyline 10%

A 70-year-old woman has suffered since 2012 from pain in her feet due to CIAP. The patient scored the pain a 6 on the NRS and characterized the pain as pins and needles, tingling, and in the same area she experienced numbness. Physical examination revealed absence of ankle jerk reflexes, hypo-esthesia for touch up to 10 cm above the ankles, presence of allodynia, and warmth cold discrimination disrupted up to 10 cm above the ankles. On the left foot and single-blind lidocaine 3% was applied and on the right foot the combination of phenytoin 5% with lidocaine 3% was applied. After 30 minutes no effect was noticed. The patient removed the creams of both feet with soap and warm water. Then a second single-blind response test followed. On the left foot the combination of phenytoin 5% with amitriptyline 10% was applied, and on the right foot the combination of phenytoin 5% with ketamine 10% cream was applied. Within 20 minutes, the patient felt pain reduction in the left foot on which phenytoin 5% with amitriptyline 10% was applied (from 6 to 5 on the NRS), though no pain reduction was noticed on the right foot. This case demonstrates the superiority of the combination of phenytoin 5% with amitriptyline 10% cream over the combination of phenytoin 5% with ketamine 10% cream and the superiority of the combination phenytoin 5% with amitriptyline 10% cream over lidocaine 3% cream with or without phenytoin 5%.

Exemplary composition 1: amitriptyline 10%/phenytoin sodium 5% cream (100 gram) (See Table 1)

TABLE 1

| Amitriptyline HCl | 10 g |
| Phenytoin sodium | 5 g |
| Cera cetomacrogolis emulsificans | 13 g |
| Decylis oleas | 17 g |
| Sorbitol 70% cristallisabile | 3.33 g |
| Acidum ascorbicum | 0.17 g |
| Citric acid monohydrate | 0.13 g |
| Aqua purificata | 51.3 g |
| | add up to 100 g |

Preparation of a pharmaceutical composition of the disclosure containing as the active pharmaceutical ingredients the first co-analgesic phenytoin sodium and the at least one further (co-)analgesic amitriptyline All compounds are accurately weighed using any approved balance. The required amount of water for a topical cream of the disclosure is measured using any approved graduated cylinder or any approved balance. The active pharmaceutical ingredients (amitriptyline HCl and phenytoin sodium) are first filtered through a fine-mesh screen of 40 mesh into a glass mortar. The oil-soluble compounds are first mixed together in a stainless steel bowl of a steering device (phase A): cera cetomacrogolis emulsificans and decylis oleas. Phase A is heated up to the melting point of the substances, usually 70° C. up to 95° C. The water-soluble compounds of the cream base (acidum ascorbicum and sorbitol 70% cristallisabile) are mixed together in another bowl and boiling water is added (phase B). When both phases are cooled down to around 70° C., phase B is then slowly poured in phase A and cooled down while steering until room temperature. Then active compounds amitriptyline HCl and phenytoin sodium are added to the mixture while steering for 10 minutes with a high-shear homogenizer. The pH can be adjusted with, for example, citric acid monohydrate to a pH between 4 and 7, or any other suitable acid is used for pH adjustment. The compositions are then packaged in, for example, 30 grams aluminum tubes and stored according to well-known methods.

Exemplary composition 2: baclofen 5%/phenytoin sodium 5% cream (100 gram) (See Table 2)

TABLE 2

| | |
|---|---|
| Baclofen | 5 g |
| Phenytoin sodium | 5 g |
| Paraffinum liquidum | 5.3 g |
| Ceteareth-20 | 1.5 g |
| White Vaseline | 13.4 g |
| Cetostearyl alcohol | 6.3 g |
| Sodium dihydrogen phosphate dehydrate | 0.3 g |
| Acidum ascorbicum 1.5% | 0.15 g |
| Sodium hydroxide | 0.05 g |
| Citric acid monohydrate | 0.13 g |
| Aqua purificata | 62.87 g: |
| | add up to 100 grams |

Exemplary composition 3: amitriptyline 10%/phenytoin 10% cream (100 gram) (See Table 3)

TABLE 3

| | |
|---|---|
| Amitriptyline HCl | 10 g |
| Phenytoin | 10 g |
| Cera cetomacrogolis emulsificans | 12 g |
| Decylis oleas | 16 g |
| Sorbitol 70% cristallisabile | 3.2 g |
| Acidum ascorbicum | 0.2 g |
| Aqua purificata | 58.6 g/add to 100 g |

Exemplary composition 4: baclofen 5%/phenytoin 5% cream (100 gram) (See Table 4)

TABLE 4

| | |
|---|---|
| Baclofen | 5 g |
| Phenytoin | 5 g |
| Cera cetomacrogolis emulsificans | 13.5 g |
| Decylis oleas | 18 g |
| Sorbitol 70% cristallisabile | 3.6 g |
| Acidum ascorbicum | 0.2 g |
| Aqua purificata | 54.7 g/add to 100 g |

Exemplary composition 5: clonidine 0.2%/phenytoin sodium 5% cream (100 gram) See Table 5)

TABLE 5

| | |
|---|---|
| Clonidine | 0.2 g |
| Phenytoin sodium | 5 g |
| Paraffinumliquidum | 5.7 g |
| Ceteareth-20 | 1.7 g |
| White Vaseline ® | 14.2 g |
| Cetostearyl alcohol | 6.8 g |
| Sodium dihydrogen phosphate dehydrate | 0.3 g |
| Acidum ascorbicum | 0.15 g |
| Sodium hydroxide | 0.05 g |
| Citric acid monohydrate | 0.13 g |
| Aqua purificata | 65.77 g: |
| | add up to 100 grams |

Exemplary composition 6: ketamine 10%/phenytoin sodium 10% cream (100 gram) (See Table 6)

TABLE 6

| | |
|---|---|
| Ketamine | 10 g |
| Phenytoin sodium | 10 g |
| Cera cetomacrogolis emulsificans | 12 g |
| Decylis oleas | 16 g |
| Sorbitol 70% cristallisabile | 3.2 g |
| Acidum ascorbicum | 0.2 g |
| Citric acid monohydrate | 0.13 g |
| Aqua purificata | 48.47 g/add to 100 g |

Exemplary composition 7: loperamide HCl 5%/phenytoin 5% cream (100 gram) (See Table 7)

TABLE 7

| | |
|---|---|
| Loperamide HCl | 5 g |
| Phenytoin | 5 g |
| Cera cetomacrogolis emulsificans | 13.5 g |
| Decylis oleas | 18 g |
| Sorbitol 70% cristallisabile | 3.6 g |
| Acidum ascorbicum | 0.2 g |
| Aqua purificata | 54.7 g/add to 100 g |

Exemplary composition 8: loperamide HCl 5%/phenytoin 10% cream (100 gram) (See Table 8)

TABLE 8

| | |
|---|---|
| Loperamide HCl | 5 g |
| Phenytoin | 10 g |
| Cera cetomacrogolis emulsificans | 12.8 g |
| Decylis oleas | 17 g |
| Sorbitol 70% cristallisabile | 3.4 g |
| Acidum ascorbicum | 0.2 g |
| Aqua purificata | 51.6 g/add to 100 g |

Exemplary composition 9: baclofen 5%/phenytoin 5% gel (100 gram) without skin penetration enhancer (See Table 9)

TABLE 9

| phenytoin 5% with baclofen 5% by weight gel (100 gram) | |
|---|---|
| Phenytoin | 5 g |
| Baclofen | 5 g |
| Carbomer 974P | 0.9 g |
| Edetate disodium | 0.09 g |
| Propylene glycol | 9 g |
| Trometamol | 0.9 g |
| Aqua purificata | 79.11 g |

Exemplary composition 10: amitriptyline 10%/phenytoin 5% petrolatum (100 gram) without skin penetration enhancer (See Table 10)

TABLE 10

| phenytoin 5% with amitriptyline in 10% by weight petrolatum (100 gram) | |
|---|---|
| Phenytoin | 5 g |
| Amitriptyline HCL | 10 g |
| Petrolatum | 85 g |

Although the foregoing methods and pharmaceutical compositions of the disclosure have been described in some detail by way of illustration and example for purposes of clarity of understanding, it is readily apparent to those of ordinary skill in the art in light of the teachings of these methods and compositions that certain changes and modifications may be made thereto without departing from the spirit or scope of the appended claims. The present disclosure is not to be limited in scope by the specific embodiments disclosed in the examples, which are intended as illustrations of a few aspects of the disclosure, and any embodiments that are functionally equivalent are within the scope of this disclosure. Indeed, various modifications of the disclosure in addition to those shown and described herein will become apparent to those skilled in the art and are intended to fall within the scope of the appended claims.

Thus, this disclosure is intended to cover any and all adaptations or variations of various embodiments and arrangements of the disclosure. Combinations of the above arrangements, and other arrangements not specifically described herein, will be apparent to those of skill in the art upon reviewing the above description. Therefore, it is intended that the disclosure is not be limited to the particular arrangement(s) disclosed as the best mode contemplated for carrying out this disclosure, but that the disclosure will include all embodiments and arrangements falling within the scope of the appended claims.

EXAMPLE

Comparative study with regard to a pharmaceutical composition comprising a first co-analgesic and at least one further (co-)analgesic as the active pharmaceutical ingredient, wherein the first co-analgesic is phenytoin, or phenytoin sodium, according to the disclosure.

Two creams were prepared according to the method of the disclosure. See for the creams, Cases 1-12, above.

In cream-1, the pharmaceutical composition comprises phenytoin and at least one further (co-)analgesic as the active pharmaceutical ingredient and the pH of the composition is about 5, according to the disclosure.

In cream-2, the pharmaceutical composition comprises phenytoin sodium and at least one further (co-)analgesic as the active pharmaceutical ingredient and the pH of the composition is about 11, according to the disclosure.

Patients receiving either cream-1, or cream-2 reported similar or the same beneficial results with regard to the reduction in peripheral neuropathic pain. Also the onset of the beneficial effect and the duration of the effect was the same or similar for both creams.

Patients did not report any side effects with regard to the skin contacted with the cream-1 or the cream-2 upon application of the creams of the disclosure.

Aspects of Small Molecule Compounds

In Table 11, some skin penetrating compounds are listed.

TABLE 11

| small-molecule compounds capable of penetrating the skin. | | |
|---|---|---|
| Active compound | Dalton | Log P |
| Phenytoin | 252 | 2.5 |
| Amitriptyline | 277 | 4.9 |
| Ketamine | 238 | 2.9 |
| Baclofen | 214 | 1.3 |
| Clonidine | 230 | 1.6 |
| Loperamide | 477 | 5.5 |
| Lidocaine | 234 | 2.6 |
| Isosorbide dinitrate | 236 | 1.3 |

Example: Pharmaceutical Compositions Comprising Phenytoin and Comprising a Skin Penetration Enhancer Case aa. Diabetic Neuropathic Pain A 69-year-old man has suffered since 2007 from peripheral neuropathic pain in both feet due to diabetes mellitus type 2. He scored his average pain as 9 on the 11-point numerical rating scale (NRS). His pain was characterized by burning, electric shocks, tingling, pins and needles, allodynia when soft stroking, and hand in hand there was numbness (anesthesia dolorosa). Especially his allodynia in his left foot was bothering him in the night, and he scored this symptom with 10 on the NRS. Pregabalin 75 mg twice daily did not have any effect. The patient was administered a compounded ketamine 10% by weight cream. The result was a reduction of allodynia to 3 on the NRS. The reduction of pain lasted 6 hours, after which he woke up and had to apply the ketamine cream again. After application of phenytoin 5% by weight cream the patient did not experience allodynia during the night anymore (0 on the NRS). Pain was reduced within 30 minutes after application and lasted for at least 12 hours.

The pharmaceutical composition containing 5% by weight phenytoin sodium in a topical cream further consisted of the skin penetration enhancer cetostearyl alcohol (6.9% by weight of the cream). The pH of the pharmaceutical composition was 11.3. The patient applied 0.5 FTU at each fore foot during each administration, i.e., in total about 0.5 gram to 0.6 gram of the cream, thus containing between about 0.025 gram to 0.03 gram of the phenytoin sodium. The patient applied the cream 2 times per day. The patient applied the cream during a period of 3 months.

Case bb. Diabetic Neuropathic Pain

A 61-year-old man, suffering since 2007 from diabetes mellitus type 2 and hypothyroidism, was treated with metformin 500 mg three times daily and Thyrax, as well as with 1000 IE vitamin D. The patient had pain in both feet and scored 8 on the NRS. His sleep quality was very much disrupted due to the neuropathic pain. The characteristics of the neuropathic pain were burning, electric, tingling and pricking sensation.

Treatment started with 5% by weight phenytoin cream, resulting for the first time since years in absence of pain during the night. The patient needed to apply the cream 3 times in 24 hours for obtaining sufficient analgesia, and analgesic effects started 1 hour after application. The cream reduced the pain with 50% to a mean value of 4 on the NRS. The pain became stable for weeks and his quality of life was much improved.

The pharmaceutical composition containing 5% by weight phenytoin sodium in a topical cream further consisted of the skin penetration enhancer cetostearyl alcohol (6.9% by weight of the cream). The pH of the pharmaceutical composition was 11.3. The patient applied 0.8 FTU at each foot during each administration, i.e., in total about 0.8 gram to 1.0 gram of the cream, thus containing between about 0.04 gram to 0.05 gram of the phenytoin sodium. The patient applied the cream 3 times per day. The patient applied the cream during a period of 4 months.

Example: Pharmaceutical Compositions Comprising Phenytoin and without Comprising a Skin Penetration Enhancer Efficacy and efficiency with regard to the treatment of peripheral neuropathic pain are demonstrated for two pharmaceutical compositions comprising phenytoin, wherein the two compositions do not comprise any skin penetration enhancer. Compounding and clinical effects of two formulations: 10% phenytoin by weight of the pharmaceutical composition, in petrolatum, and 10% phenytoin by weight of the pharmaceutical composition, in carbomer gel.

To compound 100 grams of phenytoin 10% petrolatum formulation (Table 12): add 10 g phenytoin powder to 30 g of petrolatum, and mix. Heat the mixture until melting point of petrolatum (around 50° C.) to ease the mixing. Mix, until no grains are present. The concentration of phenytoin in the homogenous paste after the first round of mixing is 40% phenytoin by weight of the composition. Subsequently, a further 70 g of petrolatum is added, heated up until melting point and mixed again until a homogenous substance is reached. Let the substance cool down while steering. The result was a homogenous white formulation, with good smearability properties that induced desired clinical effects, as described below for Case cc.

To compound phenytoin 10% gel (Table 13), the following protocol was applied for preparing a pharmaceutical composition without skin penetration enhancer: mix in one jar carbomer 974P, edetate disodium and trometamol (powder mix). Mix in another jar aqua purificata with propylene glycol. Disperse the powder mix in the liquid aqua purificata/propylene glycol mix. Allow swelling time of 15 minutes. Add phenytoin powder. Mix all ingredients.

Case cc. CIAP

A 73-year-old man has suffered from CIAP with complaints of burning pain in the lower legs, especially the feet. The average pain score, characterized as burning and pins and needles, was 7 to 8 on the NRS. The pain aggravated when sitting and lying in bed.

During the consultation, he experienced burning feet and scored his pain as 3 on the NRS. A single-blind placebo response test was performed. On the right foot placebo cream (1 FTU) was applied and on the left foot the phenytoin 10% petrolatum (1 FTU) as described here above (Table 12), was applied. The information given by the physician was: "One topical formulation can help to lessen your suffering without knowing how it exactly works. The other topical formulation I would like to offer you to test for the other foot, the working mechanism is clearer. After 30 minutes I will come back to evaluate the effect of both topical formulations."

After 2 minutes the analgesic effect of the phenytoin 10% petrolatum was noticed. He scored the pain in his left foot as 0.5 on the NRS and the right foot (placebo) as 2.5 on the NRS. Clearly, phenytoin 10% petrolatum had a more pronounced pain reduction of 2.5 points on the NRS compared to placebo, which only led to a pain reduction of 0.5 point on the NRS. Subsequently, phenytoin 10% cream comprising a skin penetration enhancer was applied on the right foot (where placebo was applied earlier) in the previous response test. Within 2 minutes the onset of pain reduction was noticeable, and when the physician returned after 20 minutes the patient reported a pain reduction of 2.5 points in the NRS. Clearly, phenytoin 10% petrolatum and phenytoin 10% cream with a penetration enhancer had comparable effects as to onset of action and same analgesic effect. The duration of the analgesic effect was for both compositions also comparable: 5 to 6 hours.

The pharmaceutical composition containing 10% by weight phenytoin in petrolatum was free of any skin penetration enhancers. The patient applied 2 FTU at both feet during each administration, i.e., about 1 gram to 1.2 gram of the topical analgesic, containing between about 0.1 gram to 0.12 gram of the phenytoin. It is intended that the patient continues using the analgesic formulation, with the instruction to apply the topical analgesic up to 4 times a day.

These results show that the presence of any skin penetration enhancer in the pharmaceutical composition comprising phenytoin is not a requirement for the pharmaceutical composition inducing a beneficial effect in the patient with regard to reducing peripheral neuropathic pain.

Case dd. CIPN

A 72-year-old man has suffered since June 2017 of CIPN, with neuropathic pain in both feet due to oxaliplatin treatment of a colon carcinoma. He scored his pain as 8 on the NRS, and the pain was characterized as: electric shocks, pins and needles, tingling, and numbness in the same area. Physical examination revealed absence of vibration sensation up to the knees, no knee and ankle jerk reflexes, hypesthesia for pinprick and allodynia in both feet. Also warmth cold discrimination was disrupted in both feet.

A single-blind placebo response test was performed. On the left foot placebo cream (1 FTU) was applied and on the right foot phenytoin 10% gel (1 FTU) was applied. The phenytoin 10% gel was the gel as here above described (Table 13). The instruction given by the physician was: "One topical formulation can help to lessen your suffering without knowing how it exactly works. The other topical formulation I would like to offer you to test for the other foot, the working mechanism is clearer. After 30 minutes I will come back to evaluate the effect of both topical formulations."

After 15 minutes the analgesic effect of the phenytoin 10% gel without skin penetration enhancer was noticed. The pain in the area on which phenytoin 10% gel was applied was reduced from 8 to 5.5 on the NRS, and the pain in the area on which placebo cream was applied was reduced from 8 to 7 on the NRS. Thus, phenytoin 10% gel clearly led to a pain reduction in neuropathic pain.

These results show that the presence of any skin penetration enhancer in the pharmaceutical composition of the disclosure is not a requirement for the pharmaceutical composition inducing a beneficial effect in the patient with regard to reducing peripheral neuropathic pain.

The pharmaceutical composition containing 10% by weight phenytoin in the topical gel without any skin penetration enhancer was applied by the patient as 2 FTU at both feet during each administration, i.e., about 1 gram to 1.2 gram of the gel, thus containing between about 0.1 gram to 0.12 gram of the phenytoin. It is intended that the patient continues using the gel during his lifespan, i.e., for the rest of her life with the instruction to apply the topical analgesic up to 6 times a day.

Constituents and their amounts in two exemplary pharmaceutical compositions comprising phenytoin wherein skin penetration enhancers are not included in the composition, which compositions are efficient and efficacious in reducing peripheral neuropathic pain when topically administered to the skin of patients.

The pharmaceutical compositions of Table 12 and Table 13 relate to the Case cc and Case dd, respectively, outlined in detail here above.

TABLE 12

| phenytoin 10% by weight petrolatum (100 gram) | |
|---|---|
| Phenytoin | 10 g |
| Petrolatum | 90 g |

TABLE 13

| phenytoin 10% by weight gel (100 gram) | |
| --- | --- |
| Phenytoin | 10 g |
| Carbomer 974P | 0.9 g |
| Edetate disodium | 0.09 g |
| Propylene glycol | 9 g |
| Trometamol | 0.9 g |
| Aqua purificata | 79.11 g |

Summary of Results of Case Aa, Bb, Cc, Dd

In the Table 14 below, a summary is provided of the efficiency of the pharmaceutical compositions comprising phenytoin and either or not further comprising one or more skin penetration enhancers, the compositions administered topically on the skin of human patients suffering from peripheral neuropathic pain.

TABLE 14

Results of treating peripheral neuropathic pain patients with pharmaceutical compositions comprising phenytoin — Case aa, bb, cc, dd

| Case | Pharmaceutical composition | Onset of pain reduction after administration | Extent of pain reduction on the NRS | Duration of pain reduction |
| --- | --- | --- | --- | --- |
| aa | 5 wt % phenytoin cream/skin penetration enhancer | 30 minutes | From 3 to 0 | At least 12 hours |
| bb | 5 wt % phenytoin cream/skin penetration enhancer | 1 hour | From 8 to 4 | About 8 hours |
| cc | 10 wt % phenytoin composition without skin penetration enhancer | 2 minutes | From 3 to 0.5 | 5 to 6 hours |
| dd | 10 wt % phenytoin gel without skin penetration enhancer | 15 minutes | From 8 to 5.5 | About 4 hours |

REFERENCES

Babaei S, Ghanbarzadeh S, Adib Z M, Kouhsoltani M, Davaran S, Hamishehkar H. Enhanced skin penetration of lidocaine through encapsulation into nanoethosomes and nanostructured lipid carriers: a comparative study. Pharmazie. 2016; 71(5):247-51.

Bailey D N. Percutaneous absorption of tricyclic antidepressants: amitriptyline, nortriptyline, imipramine, and desipramine. J Anal Toxicol. 1990; 14(4):217-218.

Baron, R., G. Hans & A. H. Dickenson (2013) Peripheral input and its importance for central sensitization. *Ann Neurol*, 74, 630-6.

Bos J D, Meinardi M M. The 500 Dalton rule for the skin penetration of chemical compounds and drugs. Exp Dermatol. 2000; 9(3):165-9.

Derry, S., P. J. Wiffen, R. A. Moore & J. Quinlan (2014) Topical lidocaine for neuropathic pain in adults. *Cochrane Database Syst Rev*, 7, Cd010958.

Finnerup, N. B., N. Attal, S. Haroutounian, E. McNicol, R. Baron, R. H. Dworkin, I. Gilron, M. Haanpaa, P. Hansson, T. S. Jensen, P. R. Kamerman, K. Lund, A. Moore, S. N. Raja, A. S. Rice, M. Rowbotham, E. Sena, P. Siddall, B. H. Smith & M. Wallace (2015) Pharmacotherapy for neuropathic pain in adults: a systematic review and meta-analysis. *Lancet Neurol*, 14, 162-73.

Gharibian, D., J. K. Polzin & J. P. Rho (2013) Compliance and persistence of antidepressants versus anticonvulsants in patients with neuropathic pain during the first year of therapy. *Clin J Pain*, 29, 377-81.

Glinn, M. A., A. J. Lickteig, L. Weber, S. Recer, M. Salske, A. Harvey, B. Rappold, J. Stensland & P. Bell (2017) Urinary Concentrations of Topically Administered Pain Medications. *J Anal Toxicol.* 41, 127-133.

Hearn, L., R. A. Moore, S. Derry, P. J. Wiffen & T. Phillips (2014) Desipramine for neuropathic pain in adults. *Cochrane Database Syst Rev*, 9, Cd011003.

Jay, G. W. & R. L. Barkin (2014) Neuropathic pain: etiology, pathophysiology, mechanisms, and evaluations. *Dis Mon*, 60, 6-47.

Jensen, T. S. (2002) Anticonvulsants in neuropathic pain: rationale and clinical evidence. *Eur J Pain*, 6 Suppl A, 61-8.

Keppel Hesselink, J. M. & D. J. Kopsky (2013) Treatment of chronic regional pain syndrome type 1 with palmitoylethanolamide and topical ketamine cream: modulation of nonneuronal cells. *J Pain Res*, 6, 239-45.

Keskin G. et al. Doxepin incorporated into a dermatologic cream: an assessment of both doxepin antipruritic action and doxepin action as an inhibitor of papules, in allergen and histamine-caused pruritus. Allergol Immunopathol (Madr) 1999; 27(5):265-70.

Korinth G, Wellner T, Schaller K H, Drexler H. Potential of the octanol-water partition coefficient (log P) to predict the dermal penetration behaviour of amphiphilic compounds in aqueous solutions. Toxicol Lett. 2012; 215(1): 49-53.

L. Lund G. Alvan A. Berlin B. Alexanderson. Pharmacokinetics of single and multiple doses of phenytoin in man. European Journal of Clinical Pharmacology March 1974, Volume 7, Issue 2, pp 81-86

McQuay, H., D. Carroll, A. R. Jadad, P. Wiffen & A. Moore (1995) Anticonvulsant drugs for management of pain: a systematic review. *Bmj*, 311, 1047-52.

Moore, R. A., P. J. Wiffen, S. Derry, T. Toelle & A. S. Rice (2014) Gabapentin for chronic neuropathic pain and fibromyalgia in adults. *Cochrane Database Syst Rev*, 4, Cd007938.

Petersen B1, Rovati S. Diclofenac epolamine (Flector) patch: evidence for topical activity. Clin Drug Investig. 2009; 29(1):1-9.

Tse S. et al. Skin permeability and pharmacokinetics of diclofenac epolamine administered by dermal patch in Yorkshire-Landrace pigs. J Pain Res. 2012; 5:401-8.

Yang, M., C. Qian & Y. Liu (2015) Suboptimal Treatment of Diabetic Peripheral Neuropathic Pain in the United States. *Pain Med*, 16, 2075-83.

The invention claimed is:

1. A pharmaceutical composition, wherein active pharmaceutical ingredients thereof consist of:
  a) a first co-analgesic selected from phenytoin or a prodrug, a stereoisomer, and/or a salt thereof, or any combination thereof;
  b) at least one further (co-)analgesic; and
  c) a pharmaceutically acceptable carrier for topical use, wherein the at least one further (co-)analgesic of b) is a combination of baclofen and amitriptyline, or loperamide and amitriptyline, or baclofen and loperamide, and/or a salt thereof, or wherein the at least one further (co-)analgesic of b) is selected from amitriptyline, baclofen, loperamide, and/or a salt thereof.

2. The pharmaceutical composition of claim 1, wherein the active pharmaceutical ingredients consist of:
   a) the first co-analgesic is selected from phenytoin and/or a salt thereof, or any combination thereof;
   b) one further (co-)analgesic; and
   c) a pharmaceutically acceptable carrier for topical use, wherein the one further (co-)analgesic of b) is selected from the group consisting of amitriptyline, baclofen, loperamide, and a salt of any thereof.

3. The pharmaceutical composition of claim 1, wherein the pharmaceutically acceptable carrier for topical use is selected from the group consisting of a cream, a gel, a dispersion, an emulsion, a foam, a mist, a mouth wash, a lotion, a salve, an ointment, an oil, a spray, an aerosol, a suppository, a suspension, a plaster, and a passive or active topical device for absorption through skin and mucous membrane.

4. The pharmaceutical composition of claim 3, wherein the pharmaceutically acceptable carrier for topical use is a cream.

5. The pharmaceutical composition of claim 1, wherein the pharmaceutically acceptable carrier for topical use comprises at least one skin penetration enhancer.

6. The pharmaceutical composition of claim 5, wherein the pharmaceutically acceptable carrier for topical use comprises at least one skin penetration enhancer selected from the group consisting of macrogol cetostearyl ether, cetostearyl alcohol, decylis oleas, and any combination thereof.

7. The pharmaceutical composition of claim 1, wherein the first co-analgesic is between 0.5% to 20% phenytoin and/or phenytoin sodium, and
   wherein the at least one further (co-)analgesic is selected from about 5% baclofen and about 5% loperamide, or
   wherein the at least one further (co-)analgesic is a combination of about 5% baclofen and about 5% amitriptyline, or loperamide 5% and baclofen 5% by weight of the pharmaceutical composition.

8. The pharmaceutical composition of claim 1, wherein the first co-analgesic is between 5% and 20% phenytoin and/or phenytoin sodium by weight of the pharmaceutical composition, and
   wherein the at least one further (co-)analgesic is selected from about 5% baclofen by weight of the pharmaceutical composition and about 5% loperamide by weight of the pharmaceutical composition, or
   wherein the at least one further (co-)analgesic is a combination of about 5% baclofen and about 5% amitriptyline by weight of the pharmaceutical composition, or loperamide 5% and baclofen 5% by weight of the pharmaceutical composition.

9. The pharmaceutical composition of claim 1, wherein the first co-analgesic is between 5% and 20% phenytoin and/or phenytoin sodium by weight of the pharmaceutical composition, and wherein the at least one further (co-)analgesic is about 10% amitriptyline by weight of the pharmaceutical composition.

10. A method for treating chronic pain, the method comprising:
    administering the pharmaceutical composition of claim 1 to an individual in need thereof,
      wherein the chronic pain is selected from the group consisting of neuropathic pain, peripheral neuropathic pain, inflammatory pain, musculoskeletal pain, pain due to muscle spasms, pain due to increased muscle tone, osteoarthritic pain, muscular headache, tension-type headache, migraine, cluster headache, atypical facial pain, referred pain, vulvodynia, proctodynia, and any combination thereof.

11. The method according to claim 10, wherein the chronic pain is peripheral neuropathic pain.

12. A method for treating chronic pain, the method comprising:
    administering a pharmaceutical composition to an individual in need thereof, wherein active pharmaceutical ingredients of the pharmaceutical composition consist of:
      a) a first co-analgesic selected from phenytoin or a prodrug, a stereoisomer, and/or a salt thereof, or any combination thereof;
      b) at least one further (co-)analgesic, and
      c) a pharmaceutically acceptable carrier for topical use,
    wherein the at least one further (co-)analgesic of b) is a combination of baclofen and amitriptyline, or loperamide and amitriptyline, or baclofen and loperamide, and/or a salt thereof, or wherein the at least one further (co-)analgesic of b) is selected from amitriptyline, baclofen, loperamide, and/or a salt thereof, and
    wherein the chronic pain is neuropathic pain selected from peripheral neuropathy caused by diabetes type 1 or 2, or induced by a noxious substance such as alcohol, due to vitamin B1, B6 and/or B12 deficiency, hypervitaminosis B6, hypothyroidism, chemotherapeutic compound such as paclitaxel or a taxane derivative, vincristine or a *vinca* alkaloid, cisplatin or a platinum derivate, drug-induced neuropathy, a compound for treatment of infectious disease such as streptomycin, didanosine or zalcitabine, a chemically toxic compound, trigeminal neuralgia, post-herpetic neuralgia, intercostal neuralgia, entrapment neuropathy such as carpal tunnel syndrome, tarsal tunnel syndrome, abdominal cutaneous nerve entrapment syndrome, small fiber neuropathy, hereditary motor and sensory neuropathies, chronic inflammatory demyelinating polyneuropathy, sciatic pain chronic idiopathic sensory neuropathy, infectious disease conditions such as post-polio syndrome, AIDS or HIV-associated, Lyme-associated, Sjögren-associated, lymphomatous neuropathy, myelomatous neuropathy, carcinomatous neuropathy, vasculitic/ischaemic neuropathy and a mono- and polyneuropathy, complex regional pain syndrome type I and II (reflex sympathetic dystrophy), central neuropathic pain such as thalamic neuropathy, spinal cord injury neuropathy, post stroke pain, multiple sclerosis neuropathy, syringomyelia, a spinal cord tumor, phantom limb pain, restless genital syndrome with pain, post-surgical scar pain including cardiac surgery and mastectomy.

13. The method according to claim 10, having a dosing frequency of the pharmaceutical composition of between once every other day and eight times daily.

14. The method according to claim 10, wherein the pharmaceutical composition is administered to the individual during a period of at least one week.

15. The method of claim 10, wherein the pharmaceutical composition is administered chronically.

16. The method according to claim 10, wherein the first co-analgesic is between 0.5% to 20% phenytoin and/or phenytoin sodium by weight of the pharmaceutical composition, and wherein the at least one further (co-)analgesic is selected from about 5% baclofen and about 5% loperamide by weight of the pharmaceutical composition, or wherein the at least one further (co-)analgesic is the combination of about 5% baclofen and about 5% amitriptyline, or loperamide 5% and baclofen 5% by weight of the pharmaceutical composition.

17. The method according to claim 10, wherein the first co-analgesic is between 5% to 20% phenytoin and/or phenytoin sodium by weight of the pharmaceutical composition, and wherein the at least one further (co-)analgesic is selected from about 5% baclofen by weight of the pharmaceutical composition and about 5% loperamide by weight of the pharmaceutical composition, or wherein the at least one further (co-)analgesic is the combination of about 5% baclofen and about 5% amitriptyline by weight of the pharmaceutical composition, or loperamide 5% and baclofen 5% by weight of the pharmaceutical composition.

18. The method according to claim 10, wherein the first co-analgesic is between 5% and 10% phenytoin and/or phenytoin sodium by weight of the pharmaceutical composition, and wherein the at least one further (co-)analgesic is selected from about 5% baclofen by weight of the pharmaceutical composition and about 5% loperamide by weight of the pharmaceutical composition, or wherein the at least one further (co-)analgesic is the combination of about 5% baclofen and about 5% amitriptyline by weight of the pharmaceutical composition, or loperamide 5% and baclofen 5% by weight of the pharmaceutical composition.

* * * * *

UNITED STATES PATENT AND TRADEMARK OFFICE
CERTIFICATE OF CORRECTION

PATENT NO. : 11,147,799 B2
APPLICATION NO. : 16/467169
DATED : October 19, 2021
INVENTOR(S) : David Jos Kopsky and Jan Marius Keppel Hesselink It is certified that error appears in the above-identified patent and that said Letters Patent is hereby corrected as shown below:

On the Title Page
In ITEM (73)  change "Jan Marius Keppel Hesselink, Amsterdam (NL);" to --Jan Marius Keppel Hesselink, Bosch en Duin (NL);--

In the Specification

| | | |
|---|---|---|
| Column 23, | Lines 1,2, | change "pharmaceutical compositions" to --pharmaceutical composition-- |
| Column 31, | Line 47, | change "Vaseline®" to --VASELINE®-- |
| Column 31, | Line 50, | change "Vaseline®" to --VASELINE®-- |
| Column 39, | Line 54, | change "and anklejerk reflexes" to --and ankle jerk reflexes-- |
| Column 41, | Line 17, | change "Vaseline®" to --VASELINE®-- |
| Column 41, | Line 60, | change "Vaseline®" to --VASELINE®-- |

In the Claims
Claim 12, Column 50, Line 14, change "(co-)analgesic, and" to --(co-)analgesic; and--

Signed and Sealed this
First Day of March, 2022

Drew Hirshfeld
*Performing the Functions and Duties of the
Under Secretary of Commerce for Intellectual Property and
Director of the United States Patent and Trademark Office*